United States Patent
Hölscher et al.

(10) Patent No.: US 10,876,067 B2
(45) Date of Patent: Dec. 29, 2020

(54) FRAGRANT MIXTURES CONTAINING ESTERS AND KETONES

(71) Applicant: Symrise AG, Holzminden (DE)

(72) Inventors: Bernd Hölscher, Halle (DE); Marc Mansfeld, Brevörde (DE); Tobias Wagner, Hellental (DE); Julia Amos, Eschershausen (DE)

(73) Assignee: Symrise AG, Holzminden (DE)

( * ) Notice: Subject to any disclaimer, the term of this patent is extended or adjusted under 35 U.S.C. 154(b) by 9 days.

(21) Appl. No.: 15/998,548

(22) PCT Filed: Feb. 15, 2016

(86) PCT No.: PCT/EP2016/053133
§ 371 (c)(1),
(2) Date: Aug. 15, 2018

(87) PCT Pub. No.: WO2017/140336
PCT Pub. Date: Aug. 24, 2017

(65) Prior Publication Data
US 2019/0136148 A1    May 9, 2019

(51) Int. Cl.
| | | |
|---|---|---|
| *A61K 8/00* | (2006.01) |
| *C11B 9/00* | (2006.01) |
| *A61K 8/35* | (2006.01) |
| *A61K 8/37* | (2006.01) |
| *A61Q 5/02* | (2006.01) |
| *A61Q 13/00* | (2006.01) |
| *A61Q 19/10* | (2006.01) |
| *C11D 3/50* | (2006.01) |
| *C11D 3/20* | (2006.01) |
| *C11D 3/00* | (2006.01) |

(52) U.S. Cl.
CPC ............... *C11B 9/003* (2013.01); *A61K 8/35* (2013.01); *A61K 8/37* (2013.01); *A61Q 5/02* (2013.01); *A61Q 13/00* (2013.01); *A61Q 19/10* (2013.01); *C11D 3/001* (2013.01); *C11D 3/2072* (2013.01); *C11D 3/2093* (2013.01); *C11D 3/50* (2013.01); *A61K 2800/591* (2013.01)

(58) Field of Classification Search
CPC .............. C11B 9/003; A61K 8/35; A61K 8/37
See application file for complete search history.

(56) References Cited

U.S. PATENT DOCUMENTS

| 4,280,934 A | 7/1981 | Schulte-Elte |
| 2013/0172429 A1* | 7/2013 | Hölscher ............... A61K 8/37 |
| | | 514/784 |

FOREIGN PATENT DOCUMENTS

| DE | 580450 C | 7/1933 |
| DE | 2729121 A1 | 1/1978 |
| EP | 0115278 A2 | 8/1984 |
| EP | 2474301 A1 | 7/2012 |
| FR | 728998 A | 7/1932 |
| GB | 391579 A | 5/1933 |
| SU | 1694571 A1 | 11/1991 |
| WO | 2009128026 A1 | 10/2009 |

OTHER PUBLICATIONS

PCT Written Opinion, English Translation, dated Jan. 2015. (Year: 2015).*
R. Horclois, Chemie et Industrie (Paris), 1934, pp. 357-363. No month available. (Abstract).*
Chapman et al., "Sterochemical evidence of dual chemoreceptors for an achiral sex phermone in Lepidoptera," Journal of the American Chemical Society 100:15 (Jul. 19, 1978), pp. 4878-4884.
Brown et al., "Reaction of Organoboranes with Ethyl Bromoacetate under the Influence of Potassium t-Butoxide. A Convenient Procedure for the Conversion of Olefins into Esters via Hydroboration," J. Am. Chem. Soc. 90:3 (Jan. 31, 1968), pp. 818-820.
Liu et al., "Sequential Reactions of Trimethylsilyldiazomethane with 4-Alkenyl Ketones and Aldehydes Catalyzed by Lewis Bases," Org. Letters 15(12) (Jun. 21, 2013), pp. 2974-2977.
Snowden, "Fragmentation of Homoalylic Alkoxides. Preparation of 1-(3'-Cyclopentenyl)-2-alkanones from 2-Substituted Bicyclo [2.2.1]hept-5-en-2-ols')," Helvetica Chimica Acta 66(4) (Jun. 15, 1983). pp. 1031-1038.
Kapferer et al., "Asymmetric Dihydroxylation of β, γ-Unsaturated Carboxylic Esters with Trisubstituted C=C Bonds-Enantioselective Synthesis of Trisubstituted γ-Butyrolactones," European Journal of Organic Chemistry 9(1) (May 1, 2006), pp. 2119-2133.
Taber et al., "A Simple Preparation of α-Diazo Esters," J. Org. Chem. 60 (1995), pp. 1093-1094.

* cited by examiner

*Primary Examiner* — John R Hardee
(74) *Attorney, Agent, or Firm* — Dilworth & Barrese, LLP

(57) ABSTRACT

The invention relates to fragrant mixtures comprising at least one compound of general formula (I), a method for producing claimed fragrant mixtures, particularly perfume oils, perfumed products containing the claimed fragrant mixture, and the use of the compound of general formula (I) to strengthen the natural freshness and/or emanation and/or to mask or reduce greasy and/or metallic notes of one or more fragrant substances that differ from the compound of formula (I).

(I)

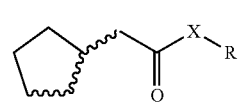

12 Claims, No Drawings

FRAGRANT MIXTURES CONTAINING ESTERS AND KETONES

FIELD OF THE INVENTION

The present invention relates to odorant mixtures comprising at least one compound of the general formula (I)

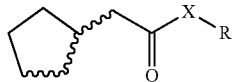
(I)

and to a method of producing odorant mixtures of the invention, especially perfume oils, perfumed products comprising the odorant mixture of the invention, and to the use of the compound of the general formula (I) for enhancing the natural freshness and/or impression and/or for masking or reducing fatty and/or metallic notes of one or more odorants other than the compound of the formula (I).

STATE OF THE ART

Green-hereby and minty odorants play an important role in perfumery. There is a constant need to emphasize (bring out) particular odor aspects of an odorant or an odorant mixture; in the case of the odorants mentioned, this is especially true of the natural freshness and impression thereof. There is likewise a constant need to mask or to reduce particular odor aspects of an odorant or an odorant mixture; in the case of the odorants mentioned, this is especially true of fatty and metallic notes.

The compounds of the general formula (I) are known per se from the prior art. However, odor descriptions can be found only for particular compounds.

An odor description of the compound ethyl cyclopent-2-enylacetate can be found in the textbook "S. Arctander, Perfume and Flavor Materials, Vol. I and II, Montclair, N.J., 1969, self-published" under number 1205. The compound ethyl cyclopent-2-enylacetale is described therein as being strong, fresh and fruity with a note of an overripe pineapple. It can likewise be inferred from the textbook that the compound is used in some aroma mixtures. Use of the compound ethyl cyclopent-2-enylacetate with flower odorants is likewise known (Symrise patent: EP 2474301 A1).

In addition, the prior art discloses that esters of the general formula:

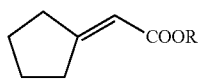

where R=hydrocarbyl radical having C1-C6 carbon atoms: branched, unbranched, saturated or unsaturated, have a fruity and flowery odor (Firmenich patent: DE-C 2729121).

An odor description of a compound of the formula (A) can be found in the prior art WO 2009 128026 A1:

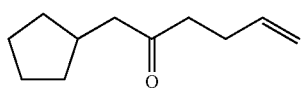
(A)

Green-hereby and minty odorants play an important role in perfumery. There is a constant need to emphasize (bring out) particular odor aspects of an odorant or an odorant mixture, in particular the natural freshness and impression thereof. There is likewise a constant need to mask or to reduce particular odor aspects of an odorant or an odorant mixture, especially fatty and metallic notes.

It was therefore an object of the present invention to emphasize or bring out particular odor aspects of particular odorants or odorant mixtures and/or to mask and/or to reduce particular odor aspects of an odorant or an odorant mixture, especially fatty and metallic notes. It was a further object of the present invention to provide odorant mixtures which can present the "green-hereby", minty odor note and additionally have positive secondary properties.

DESCRIPTION OF THE INVENTION

This object is achieved by odorant mixtures comprising a compound (a) of the general formula (I):

(I)

where, for the compound of the formula (I) or each compound of the formula (I), X is an oxygen atom or a methylene group, with the provisos that
(i) none or one of the three wavy lines denotes a double bond and the other wavy lines each denote a single bond, and
(ii) R is a linear or branched, cyclic, saturated or unsaturated hydrocarbyl radical having 1 to 5 carbon atoms.

In a preferred embodiment of the odorant mixtures of the invention, the compounds (a) of the general formula (I) are selected from compounds of the formula (Ia) or (Ib), or mixtures thereof.

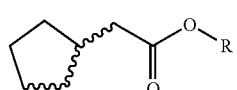
(Ia)

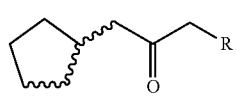
(Ib)

where, for the compound of the formula (Ia) or (Ib) or each compound of the formula (Ia) or b),
(i) none or one of the three wavy lines denotes a double bond and the other wavy lines each denote a single bond, and
(ii) R is a linear or branched, cyclic, saturated or unsaturated hydrocarbyl radical having 1 to 5 carbon atoms.

Preferably, in the case of mixtures, the compounds (Ia) and (Ib) are used in a ratio of 1:99 to 99:1, preferably 20:80 and 40:60, more preferably 30:70 and 70:30.

It has been found that, surprisingly, compounds of the general formula (I) and especially of the formula (Ia) and/or (Ib) have novel odor profiles that go in the direction of apple, pear, pineapple, banana and strawberry.

In a further embodiment, the odorant mixtures of the invention further comprise one or more further odorants (b), preferably having a green-hereby and minty odor note, from the group consisting of ketones and nitriles having a molar mass of 120 g/mol to 210 g/mol, preferably 140 g/mol to 170 g/mol; and/or one or more odorants from the group consisting of aldehydes and esters having a molar mass in the range from 190 g/mol to 250 g/mol.

In a further embodiment, the odorant mixtures of the invention further comprise one or more further odorants (c) which function as base note, selected from the group consisting of ketones and esters or lactones having a molar mass in the range from 220 g/mol to 320 g/mol.

It has advantageously been found that compounds of the formula (I), especially compounds of the formula (Ia) and/or (Ib), together with odorants b) and c) can present the "green-hereby", minty fragrance note.

In such an odorant mixture of the invention, the mass ratio of the total amount of odorants (b) to the compound(s) (a) is preferably not less than 99:1, more preferably not less than 99.9:0.1, especially preferably not less than 99.999:0.001; preferably 95:5; and/or the mass ratio of the total amount of odorants (c) to the compound(s) (a) is not less than 99:1, preferably not less than 99.9:0.1, more preferably not less than 99.999:0.001; based in each case on the total amount of all odorants in the individual groups of compounds (a), (b) and (c), based on the overall odorant mixture.

A further advantage of the odorant mixture of the invention is its high odor intensity at comparatively low dosage. Moreover, the "green-hereby", minty note is perceived particularly rapidly.

Preferably, odorant mixtures of the invention are perfume oils.

A further aspect of the present invention is therefore the use of the odorant mixtures of the invention as perfume oil.

A further aspect of the present invention is the use of the odorant mixtures of the invention for generation, imparting, modification or enhancement of a fruity odor in the direction of apple, pear, pineapple, banana and strawberry.

Preparation of Compounds of the Formula (I)

Compounds of the general formula (I) can be synthesized, for example, according to DE2729121, EP 2474301 or be prepared by a Reformatsky synthesis with subsequent elimination of water or by esterification of the corresponding acid or transesterification of the corresponding methyl esters:

The saturated compounds of the general formula (I) are arrived at by hydrogenation of the unsaturated esters.

Compounds of the formula (I) or (Ib) are likewise arrived at via a Carroll rearrangement or Claisen rearrangement (see formula scheme).

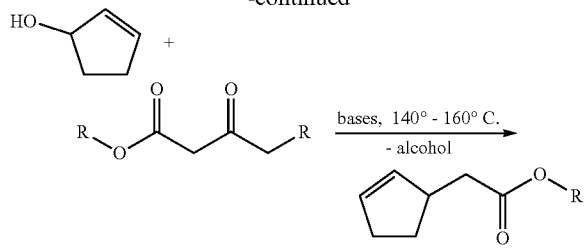

-continued

The saturated compounds of the general formula (Ib) are arrived at by hydrogenation of the unsaturated ketones.

Compounds of the General Formula (I)

Preferably, compounds (a) of the general formula (I) are selected from compounds of the formula (Ia) and/or (Ib).

In this case, the compounds are more preferably selected from the group consisting of:

methyl 2-cyclopent-2-en-1-ylacetate (compound II)

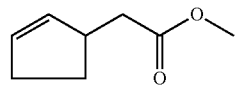

ethyl 2-cyclopent-2-en-1-ylacetate (compound III)

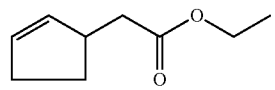

propyl 2-cyclopent-2-en-1-ylacetate (compound IV)

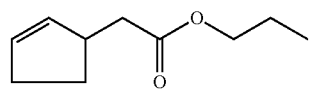

isopropyl 2 cyclopent-2-en-1-ylacetate (compound V)

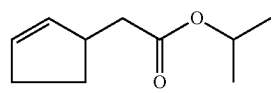

allyl 2-cyclopent-2-en-1-ylacetate (compound VI)

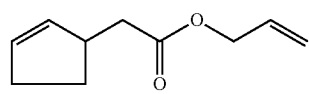

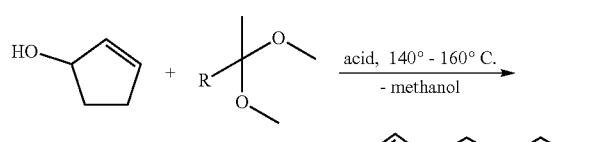

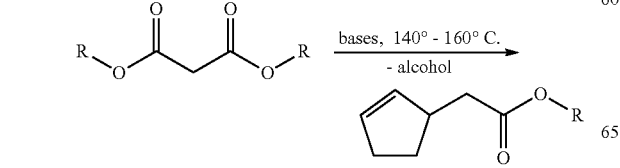

isopentyl 2-cyclopent-2-en-1-ylacetate (compound VII)

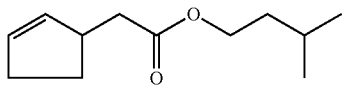

cyclopentyl 2-cyclopent-2-en-1-ylacetate (compound VIII)

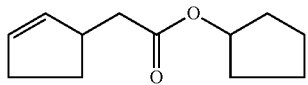

[(E)-but-2-enyl]2-cyclopent-2-en-1-ylacetate (compound IX)

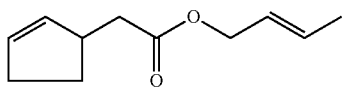

cyclopropylmethyl 2-cyclopent-2-en-1-ylacetate (compound X)

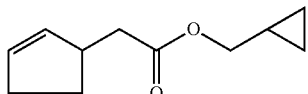

1,2-dimethylpropyl 2-cyclopent-2-en-1-ylacetate (compound XI)

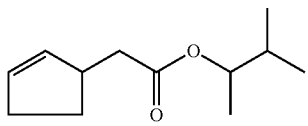

ethyl 2-(cyclopenten-1-yl) acetate (compound XII)

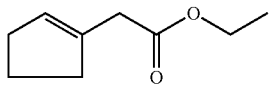

methyl 2-cyclopentylideneacetate (compound XIII)

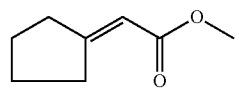

methyl 2-cyclopentylacetate (compound XIV)

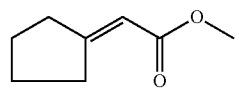

propyl 2-cyclopentylacetate (compound XV)

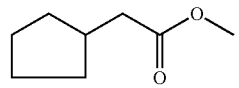

allyl 2-cyclopentylacetate (compound XVI)

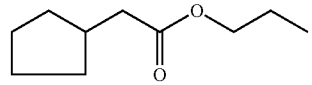

isopropyl 2-cyclopentylacetate (compound XVII)

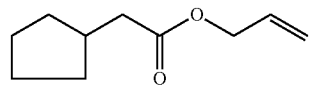

[(E)-but-2-enyl]2-cyclopentylacetate (compound XVIII)

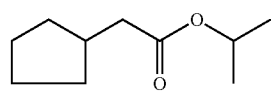

3-methylbut-2-enyl 2-cyclopent-2-en-1-ylacetate (compound XIX)

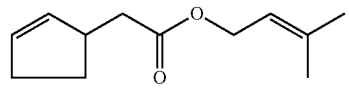

ethyl 2-cyclopentylacetate (compound XX)

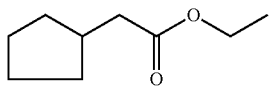

1-cyclopent-2-en-1-ylpropan-2-one (compound XXI)

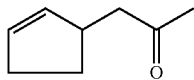

1-cyclopent-2-en-1-ylhexan-2-one (compound XXII)

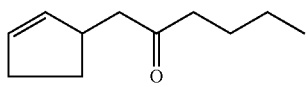

1-cyclopent-2-en-1-ylpent-4-en-2-one (compound XXIII)

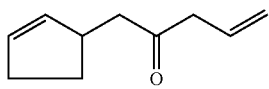

(E)-1-cyclopent-2-en-1-ylpent-3-en-2-one (compound XXIV)

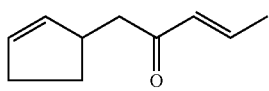

(Z)-1-cyclopent-2-en-1-ylpent-3-en-2-one (compound XXV)

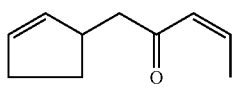

More preferably, the compounds (Ia) and (Ib) are selected from the compounds II, VI, VII, XII, XIV, XV, XVI, XX or XXIII or mixtures thereof.

Odorants (b)

Preferably, odorants (b) in the odorant mixtures of the invention are selected from the group consisting of ketones, nitriles having a molar mass of 120-210 g/mol, preferably 140 g/mol to 200 g/mol, and/or aldehydes and esters having a molar mass of preferably 110 g/mol to 250 g/mol, preferably 120 g/mol to 200 g/mol.

Preferably, odorants (b) have a green-hereby and minty odor note. Such odorants (b) based on ketones, nitriles and/or aldehydes and esters are known to the person skilled in the art.

Preference is given to odorant mixtures of the invention, preferably perfume oils, wherein odorants (b) comprise preferably two, three, four, five or more different odorant compounds.

Preferably, in an odorant mixture of the invention, the mass ratio of the total amount of odorants (b) to the compound(s) of the general formula (I), especially of the formula (Ia) and/or (Ib), is not less than 99:1, preferably not less than 99.9:0.1, more preferably not less than 99.999: 0.001, based in each case on the total amount of all odorants in the individual groups of compounds (a) and (b), based on the overall odorant mixture.

In studies, it has been found that these mass ratios are particularly advantageous since the intrinsic odor of the compound(s) of the general formula (I), especially of the formula (Ia) and/or (Ib), is regularly barely still perceptible, if at all, but the presence of the compound(s) of the general formula (I) and especially of the formula (Ia) and/or (Ib) has a positive effect on the overall fragrance note of the odorant mixture of the invention. It is particularly surprising that the compound(s) of the general formula (I), especially of the formula (Ia) and/or (Ib), even in low concentrations, has an effect on the freshness and impression of the odorant mixture without bringing about or emphasizing a fruity odor to a relevant degree.

Particular preference is given to odorant mixtures of the invention, preferably perfume oils of the invention, wherein the odorant(s) (b) are selected from the group consisting of Cantryl, Peonile, Parmanyl, menthone, Frescomenthe, isooctanone, tolylacetaldehyde, phenylacetaldehyde, Cyclogalbanate, ethyl cinnamate or mixtures thereof.

Preference is given to odorant mixtures of the invention, preferably perfume oils of the invention, wherein the one, more than one or all odorant(s) (b) each have a molar mass in the range from 140 to 200 g/mol.

Very particular preference is given to odorant mixtures of the invention, preferably perfume oils of the invention, in which the odorant (b) is a ketone.

Surprisingly, the sensory properties of odorants (b) are positively influenced by combination with an amount of the compound(s) of the general formula (I) and especially of the formula (Ia) and/or (Ib). In the individual case, the sensory Impression is shifted in the direction of natural, fresh, a stronger impression, less fatty and/or less metallic, although other sensory effects were of course also observed in the individual case. More detailed odor descriptions can be found in the appended examples.

Odorants (c)

Preferably, odorants (c) in the odorant mixtures of the invention, preferably perfume oils, are selected from the group consisting of ketones, esters/lactones and acetals having a molar mass in the range from 220 g/mol to 320 g/mol.

Preference is given to odorant mixtures of the invention, preferably perfume oils, wherein odorants (c) include preferably two, three, four, five or more different odorant compounds, for example Globalide, Globanone, Macrolide, Iso E Super, Vertofix, ambrettolide, ethylene brassylate and ambrocenide.

The odorants (c) function as base notes of an odorant mixture of the invention or of a perfume oil of the invention.

Preferably, in an odorant mixture of the invention, the mass ratio of the total amount of odorants (c) to the compound(s) of the general formula (I), especially of the formula (Ia) and/or (Ib), is not less than 99:1, preferably not less than 99.9:0.1, more preferably not less than 99.999: 0.001.

Studies have shown that these mass ratios are particularly advantageous since the intrinsic odor of the compound(s) of the general formula (I), especially of the formula (Ia) and/or (Ib) is regularly barely still perceptible, if at all, but the presence of the compound(s) of the general formula (I) and especially of the formula (Ia) and/or (Ib) has a positive influence on the overall fragrance note of the odorant mixture of the invention. It is particularly surprising that the compound(s) of the general formula (I), especially of the formula (Ia) and/or (Ib), even in low concentrations, has an effect on the freshness and impression of the odorant mixture without bringing about or emphasizing a fruity odor to a relevant degree.

Examples of odorants (c) having a molar mass in the range from 190 g/mol to 250 g/mol are known to those skilled in the art and can be found, for example, in S. Arctander, Perfume and Flavor Materials, Vol. I and II, Montclair, N.J., 1969, self-published or H. Surburg, J. Panten, "Common Fragrance and Flavor Materials", 5th Ed., Wiley-VCH, Weinheim 2006.

Particular preference is given to odorant mixtures of the invention, preferably perfume oils of the invention, wherein the odorant(s) (c) are selected from the group consisting of methyl dihydrojasmonate, benzyl salicylate, cis-3-hexenyl salicylate, isoamyl salicylate, hexyl salicylate, cedryl acetate, decahydro-beta-naphthyl acetate, 4,7-methano-3a,4,5,6,7,7a-hexahydro-5(-6)-indenyl acetate, allyl 3-cyclohexyl propionate, allyl cyclohexyloxyacetate, benzyl benzoate, benzyl cinnamate, oxacyclopentadecan-2-one, (12E/Z)-1-oxacyclopentadec-12-en-2-one, (12/13E/Z)-1-oxacyclohexadec-12/13-en-2-one, oxacyclohexadecan-2-one, 3-methylcyclopentadecanone, 1,3,4,6,7,8-hexahydro-4,6,6,7,8,8-hexamethyl cyclopenta[g]-2-benzopyran, 2-[1-(3,3-dimethylcyclohexyl)ethoxy]-2-methyl-,1-propanoate, 1,4-dioxacycloheptadecane-5,17-dione,
3-methylcyclopentadecanone, 8-cyclohexadecen-1-one, 3a,6,6,9a-tetramethyldodecahydronaphtho[2,1-b]furan,
alpha-irone, beta-irone, alpha-n-methylionone, beta-n-methylionone, alpha-isomethylionone, beta-isomethylionone and allylionone.

Surprisingly, the sensory properties of odorants (c) are positively influenced by combination with (an amount of) odorants (b) and compound(s) of the general formula (I), especially of the formula (Ia) and/or (Ib). In the individual case, the sensory impression is shifted in the direction of natural, fresh, a stronger impression, less fatty and/or less metallic, although other sensory effects were of course also observed in the individual case. More detailed odor descriptions can be found in the appended examples.

The present invention further provides a method of producing an odorant mixture of the invention, preferably perfume oils, characterized in that a compound (a) of the general formula (I)

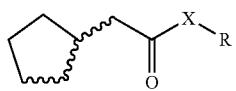
(I)

and are mixed with
(b) at least one further odorant (b), preferably having a green-hereby and minty odor note, from the group consisting of ketones and nitriles having a molar mass of 120 g/mol to 210 g/mol, preferably 140 g/mol to 200 g/mol, and/or
one or more odorants (b) from the group consisting of aldehydes and esters having a molar mass in the range from 110 g/mol to 250 g/mol, preferably 120 g/mol to 200 g/mol and/or
(c) one or more further odorants (c) selected from the group consisting of ketones and esters or lactones having a molar mass in the range from 190 g/mol to 250 g/mol.

Preference is given to odorant mixtures comprising:
(a) compounds VII and XVI, and
(b) Cantryl, menthone, phenylacetaldehyde, ethyl cinnamate, and
(c) methyl dihydrojasmonate, benzyl benzoate, benzyl cinnamate, oxacyclopentadecan-2-one, (12E/Z)-1-oxacyclopentadec-12-en-2-one, (12/13E/Z)-1-oxacyclohexadec-12/13-en-2-one, oxacyclohexadecan-2-one, 3-methylcyclopentadecenone, 1,3,4,6,7,8-hexahydro-4,6,6,7,8,8-hexamethyl-3-methylcyclopentadecanone, 8-cyclohexadecen-1-one, 3a,6,6,9a-tetramethyldodecahydronaphtho[2,1-b]furan, alpha-n-methylionone, beta-isomethylionone and allylionone.

Preference is further given to odorant mixtures comprising:
(a) compounds II and XXII, and
(b) armanyl, menthone, Frescomenthe, phenylacetaldehyde, Cyclogalbanate, and
(c) methyl dihydrojasmonate, benzyl salicylate, cis-3-hexenyl salicylate, 4,7-methano-3a,4,5,6,7,7a-hexahydro-5(-6)-indenyl acetate, oxacyclopentadecan-2-one, (12E/Z)-1-oxacyclopentadec-12-en-2-one, 2-[1-(3,3-dimethylcyclohexyl)ethoxy]-2-methyl-,1-propanoate, 1,4-dioxacycloheptadecane-5,17-dione, beta-isomethylionone and allylionone.

A further preferred odorant mixture comprises
(a) compounds XIV and XXIII, and
(b) Peonile, Parmanyl, isooctanone, tolylacetaldehyde, phenylacetaldehyde, and
(c) allyl-3-cyclohexylpropionate, allyl cyclohexyloxyacetate, benzyl benzoate, benzyl cinnamate, oxacyclopentadecan-2-one, (12E/Z)-1-oxacyclopentadec-12-en-2-one, (12/13E/Z)-1-oxacyclohexadec-12/13-en-2-one, 2-[1-(3,3-dimethylcyclohexyl)ethoxy]-2-methyl-4-propanoate, 1,4-dioxacycloheptadecane-5,17-dione, 3-methylcyclopentadecanone, 8-cyclohexadecen-1-one, 3a,6,6,9a-tetramethyldodecahydronaphtho[2,1-b]furan, alpha-irone, beta-irone, beta-n-methylionone, beta-isomethylionone and allylionone.

A further preferred odorant mixture comprises
(a) compounds XV and XXII, and
(b) menthone, isooctanone, phenylacetaldehyde, and
(c) methyl dihydrojasmonate, benzyl salicylate, cedryl acetate, benzyl cinnamate, oxacyclopentadecan-2-one, 3-methylcyclopentadecanone, 8-cyclohexadecen-1-one, alpha-n-methylionone.

A further preferred odorant mixture comprises
(a) compounds XX and XXI, and
(b) isooctanone, tolylacetaldehyde, phenylacetaldehyde, ethyl cinnamate, and
(c) benzyl salicylate, isoamyl salicylate, hexyl salicylate, cedryl acetate, allyl cyclohexyloxyacetate, benzyl benzoate, oxacyclohexadecan-2-one, 3-methylcyclopentadecenone, 8-cyclohexadecen-1-one, 3a,6,6,9a-tetramethyldodeca hydronaphtho[2,1-b]furan, alpha-irone, beta-irone, beta-iso methylionone.

A further preferred odorant mixture comprises
(a) compounds VI, XIV, and XX, and
(b) menthone, isooctanone, phenylacetaldehyde, and
(c) benzyl salicylate, isoamyl salicylate, hexyl salicylate, cedryl acetate, allyl cyclohexyloxyacetate, benzyl benzoate, oxacyclohexadecan-2-one.

These preferred odorant mixtures may of course comprise further odorants that are not covered by one of the odorant groups (a), (b) and (c) in order to refine the desired odor note.

Odorant mixtures of the invention, especially perfume oils of the invention, may be used in liquid form, undiluted form or diluted with a solvent for perfuming or aromatization. Suitable solvents for this purpose are especially ethanol, glycerol, 1,2-propylene glycol, 1,2-butylene glycol, dipropylene glycol, diethyl phthalate, triethyl citrate, isopropyl myristate and triacetin.

Preference is given to combining odorant mixtures of the invention, preferably perfume oils of the invention, with further constituents. Preferred further constituents are selected from the group consisting of:

preservatives, preferably those specified in US 2006/0089413, abrasives, antiacne compositions and compositions for sebum reduction, preferably those specified in WO 2008/046791, compositions to counteract skin aging, preferably those specified in WO 2005/123101, antibacterials, anticellulite compositions, antidandruff compositions, preferably those specified in WO 2008/046795, inflammation inhibitors, irritation inhibitors, antiirritants (anti-inflammatory, irritation-inhibiting and irritation-preventing compositions), preferably those specified in WO 2007/042472 and US 2006/0089413, antimicrobials, preferably those specified in WO 2005/123101, antioxidants, preferably those specified in WO 2005/123101, astringents, antiseptics, antistats, binders, buffers, carrier materials, preferably those specified in WO 2005/123101, chelating agents, preferably those specified in WO 2005/123101, cell stimulants, cleansers, care compositions, hair removal compositions, surface-active substances, deodorants and antiperspirants, preferably those specified in WO 2005/123101, plasticizers, emulsifiers, preferably those specified in WO 2005/123101, enzymes, essential oils, preferably those specified in US 2008/0070825, insect repellents, preferably those specified in WO 2005/123101, fibers, film formers, fixatives, foam formers, foam stabilizers, substances for prevention of foaming, foam boosters, fungicides, gelating compositions and gel-forming compositions, preferably those specified in WO 2005/123101, haircare compositions, hair shaping compositions, hair straightening compositions, moisture regulators (moisture-donating, moistening and/or humectant substances), preferably those specified in WO 2005/123101, osmolytes, preferably those specified in WO 2005/123101, compatible solutes, preferably those specified in WO 01/76572 and WO 02/15686, bleaching compositions, strengthening compositions, stain removers, optical brighteners, impregnators, soil repellents, friction reducers, lubricants, moisture creams, ointments, opacifiers, plastifying compositions, concealers, polishes, brighteners, polymers, preferably those specified in WO 2008/046676, powders, proteins and protein hydrolyzates, preferably those specified in WO 2005/123101 and WO 2008/046676, refatting compositions, abrasives, skin-calming compositions, skin cleansing compositions, skincare compositions, skin repair agents, preferably comprising cholesterol and/or fatty acids and/or ceramides and/or pseudoceramides, preferably those specified in WO 2006/053912, skin lighteners, preferably those specified in WO 2007/110415, skin protection compositions, skin-softening compositions, skin-cooling compositions, preferably those specified in WO 2005/123101, skin-warming compositions, preferably those specified in WO 2005/123101, stabilizers, UV absorbers and UV filters, preferably those specified in WO 2005/123101, benzylidene-beta-dicarbonyl compounds, preferably those specified in WO 2005/107692, alpha-benzoylcinnamonitriles, preferably those specified in WO 2006/015954, AhR receptor antagonists, preferably those specified in WO 2007/128723 and WO 2007/060256, laundry detergents, fabric softeners, suspending agents, skin tanning compositions, preferably those specified in WO 2006/045760, thickeners, vitamins, preferably those specified in WO 2005/123101, oils, waxes and fats, preferably those specified in WO 2005/123101, phospholipids, preferably those specified in WO 2005/123101, fatty acids (saturated fatty acids, mono- or polyunsaturated fatty acids, α-hydroxy acids, polyhydroxy fatty acids), preferably those specified in WO 2005/123101, liquefiers, dyes and color protection compositions, and also pigments, preferably those specified in WO 2005/123101, anticorrosives, aromas and flavorings, and further additional odorants, preferably those listed in S. Arctander, Perfume and Flavor Chemicals, self-published, Montclair, N.J., 1969 and Surburg, Panten, Common Fragrance and Flavor Materials, 5th Edition, Wiley-VCH, Weinheim 2006, especially the further odorants explicitly specified in US 2008/0070825 that are not already part of the constituents (b) and (c) of an odorant mixture of the invention or of a perfume oil of the invention, alcohols and polyols, preferably those specified in WO 2005/123101, surfactants, preferably those specified in WO 2005/123101, animal extracts, yeast extracts, extracts from algae or microalgae, electrolytes, liquefiers, organic solvents, preferably those specified in WO 2005/123101, or silicones and silicone derivatives, preferably those specified in WO 2008/046676. However, compounds, by the definition of constituents (b) and/or (c), irrespective of their purpose, are assigned to these constituents; see above for exceptions for particular solvents.

In addition, odorant mixtures of the invention, especially perfume oils of the invention, may have been adsorbed on a carrier which ensures both fine distribution of the odorants present therein in the product and a controlled release on use thereof. Carriers of this kind may be porous inorganic materials such as low-density sulfate, silica gels, zeolites, gypsums, clays, clay granules, aerated concrete, etc., or organic materials such as woods, cellulose-based substances, sugars, dextrins (e.g. maltodextrin), or plastics such as PVC, polyvinylacetates or polyurethanes. The combination of the odorant mixture of the invention and carrier constitutes an illustrative product of the invention.

Odorant mixtures of the invention, especially perfume oils of the invention, may also be in microencapsulated form, in spray-dried form, in the form of inclusion complexes or in the form of extrusion products (i.e. products of the invention) and be added in this form, for example, to a product to be perfumed.

If appropriate, the properties of the compositions thus modified may be further optimized with regard to more controlled fragrance release by "coating" with suitable materials, for which purpose preference is given to using waxy polymers, for example polyvinyl alcohols. The resulting products are again products of the invention.

The microencapsulation of the odorant mixtures of the invention, preferably of the perfume oils of the invention, can be effected, for example, by what is called the coacervation method with the aid of capsule materials, for example composed of polyurethane-like substances or soft gelatins. The spray-dried odorant or aroma compositions may be produced, for example, by spray-drying an emulsion or dispersion comprising the odorant mixture of the invention, preferably a perfume oil, in which case the carrier substances used may be modified starches, proteins, dextrin and vegetable gums. Inclusion complexes may be produced, for example, by introducing dispersions of the odorant mixture of the invention, preferably a perfume oil of the invention, and cyclodextrins or urea derivatives into a suitable solvent, for example water. Extrusion products may be obtained by fusing an odorant mixture of the invention, preferably a perfume oil of the invention, with a suitable waxy substance and by extrusion with subsequent solidification, optionally In a suitable solvent, e.g. isopropanol.

Surprisingly, compounds of the formula (I), especially compound(s) (Ia) and/or (Ib) in odorant mixtures with odorants (b), have the effect that particular odor aspects of the odorant(s) (b) are emphasized or brought out and/or masked or reduced. Especially fatty and metallic notes of the odorants of components (b) are effectively masked or reduced by compounds of the formula Id (I), especially compound(s) (Ia) and/or (Ib).

Odorants (b), as already described above, preferably have a green-hereby and minty odor note, and are selected from the group consisting of ketones and nitriles having a molar mass of 120 g/mol to 210 g/mol, preferably 140 g/mol to 170 g/mol; and/or one or more odorants from the group consisting of aldehydes and esters having a molar mass in the range from 190 g/mol to 250 g/mol.

Therefore, a further aspect of the present invention is a method of enhancing the natural freshness and/or impression and/or of masking or reducing fatty and/or metallic notes of one or more compound(s) of the general formula (I) of different odorants; especially of the odorants other than formula (Ia) and/or (Ib), having a green-hereby and/or minty odor note, comprising the following step:

mixing of the compound(s) of the general formula (I), especially of the odorants other than formula (Ia) and/or (Ib), with an amount of compound of the formula (I), especially (Ia) and/or (Ib), sufficient to enhance the natural freshness and/or impression of the odorants other than compound(s) of the general formula (I), especially the odorants other than formula (Ia) and/or (Ib), and/or to mask or to reduce fatty and/or metallic notes.

In the present process of the invention, the odorant(s) other than the compound of the formula (I), especially the odorant(s) other than formula (Ia) and/or (Ib), is/are selected from b) at least one further odorant, preferably having a green-hereby and minty odor note, from the group consisting of ketones and nitriles having a molar mass of 120 g/mol to 210 g/mol, preferably 140 g/mol to 170 g/mol; and/or one or more odorants from the group consisting of aldehydes and esters having a molar mass in the range from 190 g/mol to 250 g/mol and/or c) one or more further odorants selected from the group consisting of ketones and esters or lactones having a molar mass in the range from 220 g/mol to 320 g/mol.

The mass ratio of the total amount of odorants (b) to the compound(s) (a) here is not less than 99:1, preferably not less than 99.9:0.1, more preferably not less than 99.999: 0.001;

and/or the mass ratio of the total amount of odorants (c) to the compound(s) (a) is not less than 99:1, preferably not less than 99.9:0.1, more preferably not less than 99.999:0.001; based in each case on the total amount of all odorants in the individual groups of compounds (a), (b) and (c), based on the overall odorant mixture.

It has been found that, surprisingly, the compounds of the formula (I), especially compounds (Ia) and/or (Ib), over and above their primary sensory properties, have additional positive secondary properties, for example high stability under particular use conditions (in alkaline media (washing powder, fabric softener, soap, shampoo etc.), high yield, high adhesion capacity, high substantivity.

Accordingly, the present invention further provides a perfumed product comprising an odorant mixture of the invention, preferably a perfume oil of the invention, as described above, in a sensorily effective amount.

A "sensorily effective amount" in the present context means that the perfumed product of the invention in operation or in use allows recognition of the sensory properties of the odorant mixture of the invention.

The proportion of the odorant mixture in the perfumed product in a perfumed product of the invention is preferably 0.01% to 10% by weight, based on the total mass of the perfumed product.

Preferred perfumed products of the invention are preferably selected from the group consisting of:

perfume extracts, eau de parfums, eau de toilettes, aftershaves, eau de colognes, pre-shave products, splash colognes, perfumed refreshing tissues, acidic, alkaline and neutral cleaning products, textile fresheners, ironing aids, liquid laundry detergents, pulverulent laundry detergents, laundry pretreatment products, laundry softeners, laundry soaps, laundry tablets, disinfectants, surface disinfectants, air fresheners, aerosol sprays, waxes and polishes, personal care products, hand creams and lotions, foot creams and lotions, hair removal creams and lotions, aftershave creams and lotions, tanning creams and lotions, haircare products, deodorants and antiperspirants, decorative cosmetics products, candles, lamp oils, incense sticks, insecticides, repellents and fuels.

Particularly preferred perfumed products of the invention are selected from the following list:

eau de parfums, eau de toilettes, aftershaves, eau de colognes, pre-shave products, splash colognes;

acidic, alkaline and neutral cleaning compositions, especially in the domestic sector, preferably floor cleaners, window glass cleaners, dishwashing detergents, bathroom and sanitary cleaners, scouring milk, solid and liquid toilet cleaners, carpet cleaners in powder and foam form, liquid detergents, pulverulent detergents, fabric softeners, surface disinfectants, especially for hard surfaces (hard surface cleaners);

personal care products, preferably solid and liquid soaps, shower gels, shampoos, shaving gels, shaving foams;

cosmetic emulsions of the oil-in-water, water-in-oil and water-in-oil-in-water type, preferably skin creams and lotions, face creams and lotions, sunscreen creams and lotions, aftersun creams and lotions, hand creams and lotions, foot creams and lotions, hair removal creams and lotions, aftershave creams and lotions, skin tanning creams and lotions, skin lightening creams and lotions;

haircare products, preferably hair sprays, hair gels, setting hair lotions, hair rinses, permanent and semipermanent hair dyes, hair tonics, hair creams and lotions;

deodorants and antiperspirants, preferably underarm sprays, roll-ons (preferably in the form of an alcoholic or non-alcoholic solution, in the form of a gel or (micro)emulsion, deodorant sticks, deodorant creams.

Particularly preferred perfumed products of the invention are washing and cleaning compositions, hygiene or care products, especially in the field of personal care and hair care or of cosmetics and in the household.

Preferred perfumed products of the invention are those in which the proportion of the odorant mixture of the invention in the perfumed product is 0.01% to 10% by weight, preferably 0.1% to 5% by weight and more preferably 0.25% to 3% by weight, based in each case on the total mass of the perfumed product. This is especially true of the aforementioned preferred products.

The invention additionally also relates to a process for producing a perfumed product, comprising the steps of:
i) providing an odorant mixture of the invention or producing an odorant mixture by a method of the invention,
ii) providing the further constituents of the perfumed product and
iii) contacting the further constituents of the perfumed product that have been provided in step ii) with a sensorily effective amount of the odorant mixture provided in step i); where the amount of the compound of the general formula (I), especially formula (Ia) and/or (Ib) is sufficient to enhance the natural freshness and/or impression of one, more than one or all odorants (b) and/or (c) and/or to mask or to reduce fatty, industrial and/or metallic notes
or
I) providing the constituents of the perfumed product that are not odorants (a), (b) or (c) of an odorant mixture of the invention
II) mixing the constituents of the perfumed product provided in step I) with odorants (b) and/or (c) of an odorant mixture of the invention, so as to result in a mixture in which the odorant(s) (b) and/or (c) are present in a sensorily effective amount,
III) contacting the mixture produced in step II) with an amount of the compound of the formula (I) or (Ia), where the amount of the compound of the general formula (I), especially formula (Ia) and/or (Ib) is sufficient to enhance the natural freshness and/or impression of one, more than one or more odorants of the odorants (b) and/or (c) and/or to mask or to reduce fatty, industrial and/or metallic notes.

Preference is given to using the odorant mixtures of the invention, preferably perfume oils, in pharmaceutical compositions or cosmetic products.

Preferably suitable here are applications on the skin. Preference is given here both to cosmetic products and pharmaceutical compositions in the form of ointments, creams, lotions, gels and pastes and sprays.

Preferably, an ointment, creme, lotion, gel or paste is understood to mean a semisolid spreadable preparation suitable for application to the skin.

Preparations of this kind may, for example, be based on an aqueous (hydrophilic) and an oily or greasy (lipophilic) component, one of which is distributed in the other in the manner of an emulsion.

They may likewise be hydrophilic creams of the O/W type or lipophilic creams of the W/O type. In addition, there are creams that cannot be assigned unambiguously either to the O/W type or to the W/O type that consist of lipophilic and hydrophilic phase distributed coherently in one another in the manner of a gel (amphiphilic cream). Structures of a multiple emulsion of the W/O/W emulsion type are also possible. The inner phase here is again in the form of an emulsion. Ultrasmall water droplets have once again been included in the inner oil phase. This type of emulsion is intended to combine the advantages of W/O emulsions and O/W emulsions in one.

Further preparations are especially ointments, which is generally a semisolid preparation of homogeneous appearance, and which is suitable for application to the skin (e.g. as ointment) or to the mucus membranes. Ointments usually serve for local administration of active ingredient or for the care and protection of the skin or mucous membranes.

Preferably, an ointment consists of a hydrophobic or hydrophilic base composed of natural or synthetic substances and may be a monophasic system (e.g. Vaseline) or polyphasic system (e.g. water-in-oil).

A further preferred preparation is the gel. Gels can be described as viscoelastic fluids. Their fluid properties are thus between those of an ideal liquid and those of an ideal solid. A gel is a finely dispersed system composed of at least one solid phase and one liquid phase. The solid phase here forms a sponge-like, three-dimensional network, the pores of which are filled by a liquid (lyogel) or a gas (xerogel). If the network is highly porous and air is the gas included, the gel is also referred to as an aerogel. Both phases penetrate one another completely (bicoherent).

Preference is likewise given to formulations in the form of pastes. A paste is a solid/liquid mixture (suspension) having a high solids content. Pastes are preferably no longer free-flowing, but firm. For example, a paste is an ointment/powder mixture, and especially a semisolid medicament form having a high content of dispersed solids ("suspension ointment" with a solids content of 30% by weight for example, pasta zinci (zinc ointment) is one such paste).

One example in which a product may be in different preparation forms is, for example, toothpaste (or cream or gel), which can be applied both in the medical and in the cosmetics sector, and is thus a broad product range. The main constituents are abrasive bodies, foam formers, wetting agents and humectants, flavorings and aromas, preservatives, and dyes and additives. In addition, tooth creams also contain active ingredients for dental prophylaxis, specifically of paradontitis and caries (fluorides).

According to the invention, active ingredients and active substances can be incorporated particularly efficiently in the above-described formulations (ointments, creams, lotions, gels and pastes) by means of the capsules of the invention, since the capsules are water-insoluble and as such are stable in the base formulation, and are destroyed only as a result of the application, preferably through mechanical shear, for example through the rubbing on the skin or cleaning of teeth, and release the active ingredients or active substances.

The odorant mixtures of the invention, preferably perfume oils, can accordingly be produced in different products.

The present invention therefore further provides personal care products, washing and cleaning compositions or perfume compositions comprising the odorant mixtures of the invention, preferably perfume oils.

Cosmetic ingredients and active ingredients that are used in the personal care products, washing and cleaning compositions of perfume compositions comprising the odorant mixtures of the invention, preferably perfume oils, are listed hereinafter. Preference is given here to the perfume oils, aromas, aroma substances, fragrances.

Cosmetic Ingredients

Preferably, cosmetic products and pharmaceutical formulations comprise a series of auxiliaries and additives. These auxiliaries and additives may also be in encapsulated form if necessary. The typical auxiliaries and additives that may be present in cosmetic products and/or pharmaceutical compositions are, for example, mild surfactants, oil bodies, emulsifiers, pearlescent waxes, coolants, bodying agents, thickeners, superfatting agents, stabilizers, polymers, silicone compounds, fats, waxes, lecithins, phospholipids, UV light protection factors, humectants, biogenic active ingredients, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and the like.

Surfactants

Surface-active substances present may be anionic, nonionic, cationic and/or amphoteric or zwitterionic surfactants, the amount of which in the agents is typically about 1% to 70% by weight, preferably 5% to 50% by weight and especially 10% to 30% by weight. Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkylsulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, for example acyl lactylates, acyl tartrates, acyl glutamates and acyl aspartates, alkyloligoglucoside sulfates, protein fatty acid condensates (in particular wheat-based plant products), and alkyl (ether) phosphates. If the anionic surfactants contain polyglycol ether chains, these may have a conventional, but preferably a narrow, homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolyzates (especially wheat-based plant products), polyol fatty acid esters, sugar esters, sorbitan esters, polysorbates and amine oxides. If the nonionic surfactants contain polyglycol ether chains, they may have a conventional, but preferably a narrow, homolog distribution. Typical examples of cationic surfactants are quaternary ammonium compounds, for exdrnple dimethyldistearylammonium chloride, and ester quats, especially quaternized fatty acid trialkanolamine ester salts. Typical examples of amphoteric or zwitterionic surfactants are alkyl betaines, alkylamido betaines, aminopropionates, aminoglycinates, imidazolinium betaines and sulfo betaines. The surfactants mentioned are exclusively known compounds. Typical examples of particularly suitable mild surfactants, i.e. surfactants that are particularly well tolerated by the skin, are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, the latter preferably based on wheat proteins.

Oil Bodies

Useful oil bodies include, for example, Guerbet alcohols based on fatty alcohols having 6 to 18, preferably 8 to 10, carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Additionally suitable are esters of linear $C_6$-$C_{22}$ fatty acids with branched alcohols, in particular 2-ethylhexanol, esters of $C_{18}$-$C_{38}$-alkylhydroxycarboxylic acids with linear or branched $C_6$-$C_{22}$ fatty alcohols, in particular dioctyl malate, esters of linear and/or branched fatty acids with polyhydric alcohols (for example propylene glycol, dimer diol or trimer triol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, in particular benzoic acid, esters of $C_2$-$C_{12}$-dicarboxylic acids with linear or branched alcohols having from 1 to 22 carbon atoms or polyols having from 2 to 10 carbon atoms and from 2 to 6 hydroxyl groups, vegetable oils, branched primary alcohols, substituted cyclohexanes, linear and branched $C_6$-$C_{22}$ fatty alcohol carbonates, for example dicaprylyl carbonate (Cetiol® CC), Guerbet carbonates based on fatty alcohols having from 6 to 18, preferably from 8 to 10, carbon atoms, esters of benzoic acid with linear and/or branched $C_6$-$C_{22}$ alcohols (e.g. Finsolv® TN), linear or branched, symmetrical or unsymmetrical dialkyl ethers having from 6 to 22 carbon atoms per alkyl group, for example dicaprylyl ether (Cetiol® OE), ring-opening products of epoxidized fatty acids with polyols, silicone oils (cyclomethicone, silicon methicone types inter olio) and/or aliphatic or naphthenic hydrocarbons, for example squalane, squalene or dialkylcyclohexanes.

Emulsifiers

Useful emulsifiers include, for example, nonionic surfactants from at least one of the following groups:

addition products of 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and alkylamines having 8 to 22 carbon atoms in the alkyl moiety;

alkyl and/or alkenyl oligoglycosides having 8 to 22 carbon atoms in the alk(en)yl moiety, and ethoxylated analogs thereof;

addition products of 1 to 15 mol of ethylene oxide onto castor oil and/or hydrogenated castor oil;

addition products of 15 to 60 mol of ethylene oxide onto castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and adducts thereof with 1 to 30 mol of ethylene oxide;

partial esters of polyglycerol (average inherent degree of condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside) and polyglucosides (e.g. cellulose) with saturated and/or unsaturated, linear or branched fatty acids having 12 to 22 carbon atoms and/or hydroxycarboxylic acids having 3 to 18 carbon atoms, and adducts thereof with 1 to 30 mol of ethylene oxide;

mixed esters of pentaerythritol, fatty acids, citric acid and fatty alcohol and/or mixed esters of fatty acids having 6 to 22 carbon atoms, methylglucose and polyols, preferably glycerol or polyglycerol;

mono-, di- and trialkyl phosphates, and mono-, di- and/or tri-PEG-alkyl phosphates and salts thereof;

wool wax alcohols;

polysiloxane-polyalkyl-polyether copolymers or corresponding derivatives;

block copolymers, for example polyethylene glycol-30 dipolyhydroxystearate;

polymeric emulsifiers, for example Pemulen types (TR-1, TR-2) from Goodrich or Cosmedia® SP from Cognis;

polyalkylene glycols; and glycerol carbonate.

Particularly suitable emulsifiers are elucidated in detail hereinafter:

Alkoxylates. The addition products of ethylene oxide and/or propylene oxide onto fatty alcohols, fatty acids, alkylphenols or with castor oil are known products which are available commercially. They are homolog mixtures having an average degree of alkoxylation that corresponds to the ratio of the amounts of ethylene oxide and/or propylene oxide and substrate with which the addition reaction is carried out. $C_{12/18}$ fatty acid mono- and diesters of addition products of ethylene oxide with glycerol are known as refatting agents for cosmetic preparations.

Alkyl and/or alkenyl oligoglycoside. Alkyl and/or alkenyl oligoglycosides and the preparation and use thereof are known from the prior art. They are especially prepared by reaction of glucose or oligosaccharides with primary alcohols having 8 to 18 carbon atoms. With regard to the glycoside radical, both monoglycosides, in which a cyclic sugar residue is glycosidically bonded to the fatty alcohol, and oligomeric glycosides having a degree of oligomerization up to preferably approximately 8 are suitable. The degree of oligomerization is a statistical average based on a conventional homolog distribution for such commercial products.

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric diglyceride, malic acid monoglyceride, malic acid diglyceride and commercial mixtures thereof which may still contain small amounts of triglyceride as a minor product from the preparation process. Likewise suitable are addition products of 1 to 30 mol, preferably 5 to 10 mol, of ethylene oxide with the partial glycerides mentioned.

Sorbitan esters. As sorbitan esters come sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan mono-hydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and commercial mixtures thereof. Also suitable are addition products of 1 to 30 mol, preferably 5 to 10 mol, of ethylene oxide with the sorbitan esters mentioned.

Polyglycerol esters. Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403) polyglyceryl dimerate isostearate and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Anionic emulsifiers. Typical anionic emulsifiers are aliphatic fatty acids having 12 to 22 carbon atoms, for example palmitic acid, stearic acid or behenic acid, and dicarboxylic acids having 12 to 22 carbon atoms, for example azelaic acid or sebacic acid.

Amphoteric and cationic emulsifiers. Further emulsifiers that may be used are zwitterionic surfactants. Zwitterionic surfactants refer to those surface-active compounds that bear at least one quaternary ammonium group and at least one carboxylate group and one sulfonate group in the molecule. Particularly suitable zwitterionic surfactants are the so-called betaines such as the N-alkyl-N,N-dimethylammoniumglycinates, for example cocoalkyldimethylammoniumglycinate, N-acylaminopropyl-N,N-dimethylammoniumglycinate, for example cocoacylaminopropyl-dimethylammoniumglycinate, and 2-alkyl-3-carboxylmethyl-3-hydroxyethylimidazolines each having 8 to 18 carbon atoms in the alkyl or acyl group, and also cocoacylaminoethyl-hydroxyethylcarboxymethylglycinate. Particular preference is given to the fatty acid amide derivative known by the CTFA name Cocamidopropyl Betaine. Ampholytic surfactants are likewise suitable emulsifiers. Ampholytic surfactants are understood to mean those surface-active compounds that contain in the molecule, in addition to a $C_{8/18}$-alkyl or -acyl group, at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having about 8 to 18 carbon atoms in the alkyl group. Particularly preferred ampholytic surfactants are N-cocoalkylaminopropionate, cocoacylaminoethylamino propionate and $C_{12/18}$-acylsarcosine. Finally, cationic surfactants are also useful emulsifiers, particular preference being given to those of the esterquat type, especially methyl-quaternized di-fatty acid triethanolamine ester salts.

Fats and Waxes

Typical examples of fats are glycerides, i.e. solid or liquid vegetable or animal products which consist substantially of mixed glycerol esters of higher fatty acids; useful waxes include natural waxes, for example candelilla wax, carnauba wax, japan wax, esparto grass wax, cork wax, guaruma wax, rice germ oil wax, sugarcane wax, ouricury wax, montan wax, beeswax, shellac wax, sperm whale oil, lanolin (wool wax), uropygial oil, ceresin, ozokerite (earth wax), petrolatum, paraffin waxes, microwaxes; chemically modified waxes (hard waxes), for example montan ester waxes, Sasol waxes, hydrogenated jojoba waxes and synthetic waxes, for example polyalkylene waxes and polyethylene glycol waxes. In addition to the fats, useful additives are also fat-like substances, such as lecithins and phospholipids. The person skilled in the art will understand the term lecithins to mean those glycero-phospholipids which are formed from fatty acids, glycerol, phosphoric acid and choline by esterification. Lecithins are therefore frequently also among experts as phosphatidylcholines (PC). Examples of natural lecithins include the cephalins, which are also referred to as phosphatidic acids and are derivatives of 1,2-diacyl-sn-glycerol-3-phosphoric acids. By contrast, phospholipids are usually understood to mean mono- and preferably diesters of phosphoric acid with glycerol (glycerol phosphates), which are generally included among the fats. In addition, sphingosines or sphingolipids are also useful.

Pearlescent Waxes

Useful pearlescent waxes include, for example: alkylene glycol esters, especially ethylene glycol distearate; fatty acid alkanolamides, especially coconut fatty acid diethanolamide; partial glycerides, especially stearic acid monoglyceride; esters of polyvalent, optionally hydroxy-substituted carboxylic acids with fatty alcohols having 6 to 22 carbon atoms, especially long-chain esters of tartaric acid; fatty substances, for example fatty alcohols, fatty ketones, fatty aldehydes, fatty ethers and fatty carbonates, which contain at least 24 carbon atoms in total, especially laurone and distearyl ether; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Coolants

Coolants are compounds which create a sensation of coolness on the skin. In general, these are menthol compounds which in addition to the main menthol structure itself selected for example from the group formed by menthol methyl ether, menthone glyceryl acetal (FEMA GRAS 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomethyl glutamate (FEMA GRAS 4006), menthoxy-1,2-propanediol (FEMA GRAS 3784), menthoxy-2-methyl-1,2-propanediol (FEMA GRAS 3849) and also the menthanecarboxylic acid esters and amides WS-3, WS-4, WS-5, WS-12, WS-14 and WS-30 and mixtures thereof.

A first important representative of these substances is monomethyl succinate (FEMA GRAS 3810). Both the succinate and the analogous monomenthyl glutarate (FEMA GRAS 4006) are important representatives of monomenthyl esters based on di- and polycarboxylic acids:

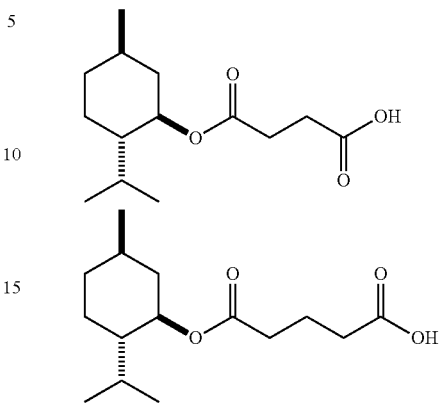

Examples of applications of these substances are to be found, for example, in publications WO 2003 043431 (Unilever) or EP 1332772 A1 (IFF).

The next important group of menthol compounds which are preferred within the context of the invention includes carbonate esters of menthol and polyols, for example glycols, glycerol or carbohydrates, for example menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives. Likewise preferred are the menthol compounds menthyl lactate (FEMA GRAS 3748=Frescolat® ML) and in particular menthone glyceryl acetal (FEMA GRAS 3807) or menthone glyceryl ketal (FEMA GRAS 3808), which is marketed under the name Frescolat® MGA. Very particularly advantageous substances among these have been found to be menthone glyceryl acetal/ketal and menthyl lactate, and also menthol ethylene glycol carbonate or menthol propylene glycol carbonate, which are marketed by the applicant under the names Frescolat® MGA, Frescolat® ML, Frescolat® MGC and Frescolat® MPC.

In the 1970s, menthol compounds having a C—C bond in the 3-position were developed for the first time, and a number of representatives of these compounds can likewise be used. These substances are referred to generally as WS types. The main structure is a menthol derivative in which the hydroxyl group has been replaced by a carboxyl group (WS-1). All further WS types, for example the preferred species WS-3, WS-4, WS-5, WS-12, WS-14 and WS-30, are derived from that structure.

Bodying Agents and Thickeners

Useful bodying agents are primarily fatty alcohols or hydroxy fatty alcohols having 12 to 22 and preferably 16 to 18 carbon atoms and, in addition, partial glycerides, fatty acids or hydroxy fatty acids. Preference is given to a combination of these substances with alkyl oligoglucosides and/or fatty acid N-methylglucamides of equal chain length and/or polyglycerol poly-12-hydroxystearates. Suitable thickeners are, for example, Aerosil types (hydrophilic silicas), polysaccharides, in particular xanthan gum, guar-guar, agar-agar, alginates and tyloses, carboxymethylcellulose and hydroxyethyl- and hydroxypropyl-cellulose, also higher molecular weight polyethylene glycol mono- and diesters of fatty acids, polyacrylates (e.g. Carbopols® and Pemulen types from Goodrich; Synthalens® from Sigma; Keltrol types from Kelco; Sepigel types from Seppic; Salcare types from Allied Colloids), polyacrylamides, polymers, polyvinyl alcohol and polyvinylpyrrolidone. Bentonites, for example Bentone® Gel VS-5PC (Rheox), which is a mixture of cyclopentasiloxane, disteardimonium hectorite and propylene carbonate, have also been found to be particularly effective. Further useful surfactants include, for example, ethoxylated fatty acid glycerides, esters of fatty acids with polyols, for example pentaerythritol or trimethylolpropane, fatty alcohol ethoxylates with narrow homolog distribution or alkyl oligoglucosides, and also electrolytes such as sodium chloride and ammonium chloride.

Superfatting Agents and Stabilizers

Superfatting agents used may be substances such as lanolin and lecithin, for example, and polyethoxylated or acylated lanolin and lecithin derivatives, polyol fatty acid esters, monoglycerides and fatty acid alkanolamides, and the latter simultaneously serve as foam stabilizers.

Stabilizers used may be metal salts of fatty acids, for example magnesium stearate or ricinoleate, aluminum stearate or ricinoleate and/or zinc stearate or ricinoleate.

UV Light Protection Factors

UV light protection factors are understood to mean, for example, organic substances (light protection filters) which are in liquid or crystalline form at room temperature and are capable of absorbing ultraviolet rays and giving off the absorbed energy again in the form of long-wave radiation, for example heat. The UV light protection factors are conventionally present in amounts of 0.1% to 5% by weight and preferably 0.2% to 1% by weight. UVB filters may be oil-soluble or water-soluble. Examples of oil-soluble substances include:

3-benzylidenecamphor or 3-benzylidenenorcamphor and derivatives thereof, for example 3-(4-methylbenzylidene)camphor described;

4-aminobenzoic acid derivatives, preferably 4-(dimethylamino)benzoic acid 2-ethylhexyl ester, 4-(dimethylamino)benzoic acid 2-octyl ester and 4-(dimethylamino)benzoic acid amyl ester;

esters of cinnamic acid, preferably 4-methoxycinnamic acid 2-ethylhexyl ester, 4-methoxycinnamic acid propyl ester, 4-methoxycinnamic acid isoamyl ester, 2-cyano-3,3-phenylcinnamic acid 2-ethylhexyl ester (octocrylene); esters of salicylic acid, preferably salicylic acid 2-ethylhexyl ester, salicylic acid 4-isopropylbenzyl ester, salicylic acid homomenthyl ester;

derivatives of benzophenone, preferably 2-hydroxy-4-methoxybenzophenone, 2-hydroxy-4-methoxy-4'-methyl benzophenone, 2,2'-dihydroxy-4-methoxybenzophenone;

esters of benzalmalonic acid, preferably 4-methoxybenzmalonic acid di-2-ethylhexyl ester;

triazine derivatives, for example 2,4,6-trianilino-(p-carbo-2'-ethyl-1'-hexyloxy)-1,3,5-triazine and Octyl Triazone or Dioctyl Butamido Triazone (Uvasorb® HEB);

propane-1,3-diones, for example 1-(4-tert-butylphenyl)-3-(4'-methemphenyl)-propane-1,3-dione;

ketotricyclo(5.2.1.0)decane derivatives.

Useful water-soluble substances include:

2-phenylbenzimidazole-5-sulfonic acid and the alkali, alkaline earth, ammonium, alkylammonium, alkanolammonium and glucammonium salts thereof;

1H-benzimidazole-4,6-disulfonic acid, 2,2'-(1,4-phenylene)bis-, disodium salt (Neo Heliopan® AP);

sulfonic acid derivatives of benzophenones, preferably 2-hydroxy-4-methoxyhenzo-phenone-5-sulfonic acid and its salts;

sulfonic acid derivatives of 3-benzylidene camphor, for example 4-(2-oxo-3-bornylidenemethyl)benzene sulfonic acid and 2-methyl-5-(2-oxo-3-bornylidene)sulfonic acid and salts thereof.

Useful typical UV-A filters especially include derivatives of benzoylmethane, for example 1-(4'-tert-butylphenyl)-3-(4'-methoxyphenyl)propane-1,3-dione, 4-tert-butyl-4'-methoxydibenzoylmethane (Parsol® 1789), 2-(4-diethylamino-2-hydroxybenzoyl)benzoic acid hexyl ester (Uvinule A Plus), 1-phenyl-3-(4'-isopropylphenyl)propane-1,3-dione, and enamine compounds. The UV-A and UV-B filters can of course also be used in mixtures. Particularly advantageous combinations consist of the derivatives of benzoylmethane, for example 4-tert-butyl-4'-methoxydibenzoylmethane (Parsol® 1789) and 2-cyano-3,3-phenylcinnamic acid 2-ethylhexyl ester (octocrylene) in combination with esters of cinnamic acid, preferably 4-methoxycinnamic acid 2-ethylhexyl ester and/or 4-methoxycinnamic acid propyl ester and/or 4-methoxycinnamic acid isoamyl ester. Such combinations are advantageously combined with water-soluble filters, for example 2-phenylbenzimidazole-5-sulfonic acid and the alkali, alkaline earth, ammonium, alkylammonium, alkanolammonium and glucammonium salts thereof.

In addition to the soluble substances mentioned, also useful for this purpose are insoluble light protection pigments, namely finely dispersed metal oxides or salts. Examples of suitable metal oxides are especially zinc oxide and titanium dioxide and, in addition, oxides of iron, zirconium, silicon, manganese, aluminum and cerium and mixtures thereof. Salts used may include silicates (talc), barium sulfate or zinc stearate. The oxides and salts are used in the form of the pigments for skincare and skin protection emulsions and decorative cosmetics. The particles here should have an average diameter of less than 100 nm, preferably between 5 and 50 nm and especially between 15 and 30 nm. They can have a spherical shape, but it is also possible to use particles that have an ellipsoid shape or a shape which otherwise differs from the spherical form. The pigments can also be present in surface-treated, i.e. hydrophilized or hydrophobized, form. Typical examples are coated titanium dioxides, for example titanium dioxide T 805 (Degussa) or Eusolex® T2000, Eusolex® T, Eusolex® T-ECO, Eusolex® T-S, Eusolex® T-Aqua, Eusolex® T-45D (all from Merck), Uvinul $TiO_2$ (BASF). Useful hydrophobic coating agents especially include silicones and in particular trialkoxyoctylsilanes or simethicone. In sunscreens, what are called micro- or nanopigments are used with preference. Preference is given to the use of micronized zinc oxide, for example Z-COTE® or Z-COTE HP1®.

Humectants

Humectants serve to further optimize the sensory properties of the composition and to regulate the moisture content of the skin. At the same time, the low-temperature stability of the preparations of the invention, especially in the case of emulsions, is increased. The humectants are typically present in an amount of 0.1% to 15% by weight, preferably 1% to 10% by weight and especially 5% to 10% by weight.

The following are among those suitable in accordance with the invention: amino acids, pyrrolidonecarboxylic acid, lactic acid and salts thereof, lactitol, urea and urea derivatives, uric acid, glucosamine, creatinine, cleavage products of collagen, chitosan or chitosan salts/derivatives, and especially polyols and polyol derivatives (e.g. glycerol, diglycerol, triglycerol, ethylene glycol, propylene glycol, butylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20), sugars and sugar derivatives (including fructose, glucose, maltose, maltitol, mannitol, inositol, sorbitol, sorbitylsilanediol, sucrose, trehalose, xylose, xylitol, glucuronic acid and salts thereof), ethoxylated sorbitol (sorbeth-6, sorbeth-20, sorbeth-30, sorbeth-40), honey and hydrogenated honey, hydrogenated starch hydrolyzates, and also mixtures of hydrogenated wheat protein and PEG-20-acetate copolymer. Glycerol, diglycerol, triglycerol and butylene glycol are preferably suitable in accordance with the invention as humectants.

Biogenic Active Ingredients and Antioxidants

Biogenic active ingredients are understood to mean, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example plum extract, Bambara nut extract and vitamin complexes.

Antioxidants interrupt the photochemical reaction chain which is initiated when UV radiation penetrates the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and also sulfoximine compounds (e.g. buthionine sulfoximine, homocysteine sulfoximine, buthionine sulfone, penta-, hexa-, hepta-thionine sulfoximine) in very small tolerable doses (e.g. μmol to μmol/kg), also (metal) chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and also coniferyl benzoate of benzoin, rutic acid and derivatives thereof, α-glycosylrutin, ferulic acid, furfurylidene glucitol, carnosine, butylhydroxytoluene, butylhydroxyanisole, nordihydroguaiac resin acid, nordihydroguaiaretic acid, trihydroxy-butyrophenone, uric acid and derivatives thereof, mannose and derivatives thereof, superoxide dismutase, zinc and derivatives thereof (e.g. ZnO, $ZnSO_4$) selenium and derivatives thereof (e.g. selenium methionine), stilbene and derivatives thereof (e.g. stilbene oxide, trans-stilbene oxide) and the derivatives of those active ingredients mentioned that are suitable in accordance with the invention (salts, esters, ethers, sugars, nucleotides, nucleosides, peptides and lipids).

Deodorants and Bacteriostatic Agents

Cosmetic deodorants counteract body odors, mask or eliminate them. Body odors arise due to the action of skin bacteria on apocrine sweat, forming malodorous degradation products. Deodorants accordingly comprise active ingredients which act as bacteriostatic agents, enzyme inhibitors, odor absorbers or odor-masking agents.

Bacteriostatic agents. Suitable bacteriostatic agents in principle include any substances which are active against Gram-positive bacteria, for example 4-hydroxybenzoic acid and its salts and esters, N-(4-chlorophenyl)-N'-(3,4-dichlorophenyl)urea, 2,4,4'-trichloro-2'-hydroxydiphenyl ether (Triclosan), 4-chloro-3,5-dimethylphenol, 2,2'-methylenebis (6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), N-alkylsalicylamides, for example N-n-octylsalicylamide or N-n-decylsalicylamide.

Enzyme inhibitors. Useful enzyme inhibitors include, for example, esterase inhibitors. They are preferably trialkyl citrates such as trimethyl citrate, tripropyl citrate, triisopropyl citrate, tributyl citrate and in particular triethyl citrate (Hydagen® CAT). The substances inhibit enzyme activity and thereby reduce odor formation. Further useful esterase inhibitors include sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester, and zinc glycinate.

Odor absorbers. Suitable odor absorbers are substances which are able to absorb and largely retain odor-forming compounds. They lower the partial pressure of the individual components and thus also reduce the rate at which they spread. What is important is that perfumes have to remain unaffected. Odor absorbers are not effective against bacteria. They comprise as the main constituent, for example, a complex zinc salt of ricinoleic acid or special, largely odor-neutral fragrances, which are known to the person skilled in the art as "fixatives", for example extracts of labdanum or styrax or specific abietic acid derivatives. Fragrances or perfume oils which, in addition to their function as odor-masking agents, impart to the deodorants their particular fragrance note act as odor-masking agents. Examples of useful perfume oils include mixtures of natural and synthetic fragrances. Natural fragrances are extracts of blossoms, stems and leaves, fruits, fruit skins, roots, woods, herbs and grasses, needles and branches, and resins and balsams. Animal raw materials are also suitable, for example civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allylcyclohexyl propionate, styrallyl propionate and benzyl salicylate. The ethers include, for example, benzyl ethyl ether, the aldehydes include, for example, the linear alkanals having 8 to 18 carbon atoms, citral, citronellal, citronellyl oxyacetaldehyde, cyclamen aldehyde, hydroxycitronellal, lilial and bourgeonal, the ketones include, for example, the ionones and methyl cedryl ketone, the alcohols include anethol, citronellol, eugenol, isoeugenol, geraniol, linalool, phenylethyl alcohol and terpineol, the hydrocarbons include mainly the terpenes and balsams. Preference is given, however, to the use of mixtures of different fragrances which together produce an appealing fragrance note. Essential oils of relatively low volatility, which are used mostly as flavor components, are also suitable as perfume oils, for example sage oil, camomile oil, clove oil, melissa oil, mint oil, cinnamon leaf oil, lime blossom oil, juniper berry oil, vetiver oil, olibanum oil, galbanum oil, labdanum oil and lavandin oil. Preference is given to the use of bergamot oil, dihydromyrcenol, lilial, lyral, citronellol, phenylethyl alcohol, α-hexyl cinnamaldehyde, geraniol, benzylacetone, cyclamen aldehyde, linalool, Boisambrene Forte, Ambroxan, indole, hedione, sandelice, lemon oil, mandarin oil, orange oil, allylamyl glycolate, cyclovertal, lavandin oil, clary sage oil, β-damascone, geranium oil bourbon, cyclohexyl salicylate, Vertofix Coeur, Iso-E-Super, Fixolide NP, evernyl, iraldeine gamma, phenylacetic acid, geranyl acetate, benzyl acetate, rose oxide, romilat, irotyl and floramat, on their own or in mixtures.

Antiperspirants. Antiperspirants reduce perspiration by influencing the activity of the eccrine sweat glands and thus counteract underarm wetness and body odor. Aqueous or water-free formulations of antiperspirants typically comprise the following ingredients:
astringent active ingredients,
oil components,
nonionic emulsifiers,
coemulsifiers,
bodying agents,
auxiliaries, for example thickeners or complexing agents, and/or
nonaqueous solvents, for example ethanol, propylene glycol and/or glycerol.

Suitable astringent antiperspirant active ingredients are in particular salts of aluminum, zirconium or zinc. Suitable active ingredients having antihydrolytic activity of this type are, for example, aluminum chloride, aluminum chlorohydrate, aluminum dichlorohydrate, aluminum sesquichlorohydrate and complex compounds thereof, for example with 1,2-propylene glycol. Aluminum hydroxyallantoinate, aluminum chloride tartrate, aluminum-zirconium trichlorohydrate, aluminum-zirconium tetrachlorohydrate, aluminum-zirconium pentachlorohyd rate and complex compounds thereof, for example with amino acids such as glycine. Oil-soluble and water-soluble auxiliaries conventional in antiperspirants may additionally be present in lesser amounts. Such oil-soluble auxiliaries may be, for example:
antiinflammatory, skin-protecting or fragrant essential oils,
synthetic skin-protecting active ingredients, and/or
oil-soluble perfume oils.

Conventional water-soluble additives are, for example, preservatives, water-soluble fragrances, agents for adjusting the pH, for example buffer mixtures, water-soluble thickeners, for example water-soluble natural or synthetic polymers, for example xanthan gum, hydroxyethylcellulose, polyvinylpyrrolidone or high molecular weight polyethylene oxides.

Antidandruff Active Ingredients

Useful antidandruff active ingredients include piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinoleic polyethoxylate, sulfur tar distillates, salicylic acid (or in combination with hexachlorophen), undecylenoic acid monoethanolamide sulfosuccinate Na salt, Lamepon® UD (protein undecylenoic acid condensate), zinc pyrithione, aluminum pyrithione and magnesium pyrithione/dipyrithione magnesium sulfate.

Insect Repellents

Useful insect repellents include N,N-diethyl-m-toluamide, 1,2-pentanediol or ethyl butylacetylaminopropionate. A suitable self-tanning agent is dihydroxyacetone. Useful tyrosine inhibitors that prevent the formation of melanin and find use in depigmenting agents include, for example, arbutin, ferulic acid, kojic acid, coumaric acid and ascorbic acid (vitamin C).

Ingredients for Oral and Dental Care Compositions

Oral and dental care compositions are understood to mean products that serve for oral and dental cleaning and care. Examples of these are toothpastes, tooth gels and the like.

Toothpastes or tooth creams are generally understood to mean gel-type or pasty preparations of water, thickeners, humectants, abrasive or cleaning bodies, surfactants, sweeteners, aroma substances, deodorizing active ingredients and also active ingredients against oral and dental diseases. All customary cleaning bodies, for example chalk, dicalcium phosphate, insoluble sodium metaphosphate, aluminum silicates, calcium pyrophosphate, finely divided synthetic resins, silicas, aluminum oxide and aluminum oxide trihydrate can be used in the toothpastes of the invention.

Preferentially suitable cleaning bodies for the toothpastes of the invention are, in particular, finely divided xerogel silicas, hydrogel silicas, precipitated silicas, aluminum oxide trihydrate and finely divided alpha-aluminum oxide or mixtures of these cleaning bodies in amounts of 15% to 40% by weight of the toothpaste. Useful humectants include primarily low-molecular-weight polyethylene glycols, glycerol, sorbitol or mixtures of these products in amounts up to 50% by weight. Suitable thickeners among those known are the thickening, finely divided gel silicas and hydrocolloids, for example carboxymethylcellulose, hydroxyethylcellulose, hydroxypropyl guar, hydroxyethyl starch, polyvinylpyrrolidone, high-molecular-weight polyethylene glycol, plant gums such as tragacanth, agar-agar, carrageen moss, gum arabic, xanthan gum and carboxyvinyl polymers (e.g. Carbopol® types). In addition to the mixtures of menthofuran and menthol compounds, the oral and dental care compositions may especially comprise surface-active substances, preferably anionic and nonionic high-foam surfactants, such as the aforementioned substances, but in particular alkylether sulfate salts, alkylpolyglucosides and mixtures thereof.

Further Customary Toothpaste Additives Are:
preservatives and antimicrobial substances, for example methyl, ethyl or propyl p-hydroxybenzoates, sodium sorbate, sodium benzoate, bromochlorophene, phenyl salicylates, thyrnol and the like;
antitartar active ingredients, e.g. organophosphates such as 1-hydroxyethane-1,1-diphosphonic acid, 1-phosphonopropane-1,2,3-tricarboxylic acid and others, which are known, for example, from U.S. Pat. No. 3,488,419, DE 2224430 A1 and DE 2343196 A1;
other anticaries substances for example sodium fluoride, sodium monofluorophosphate, tin fluoride;
sweetening agents, for example saccharin sodium, sodium cyclamate, sucrose, lactose, maltose, fructose or aspartame, (L-aspartyl-L-phenylalanine methyl ester), stevia extracts or the sweetening components thereof, in particular rebaudiosides;

additional flavorings for example eucalyptus oil, aniseed oil, fennel oil, caraway oil, methyl acetate, cinnamaldehyde, anethol, vanillin, thymol and also mixtures of these and other natural and synthetic flavorings;

pigments for example titanium dioxide;

dyes;

buffer substances for example primary, secondary or tertiary alkali metal phosphates or citric acid/sodium citrate;

wound-healing substances and antiinflammatories, for example allantoin, urea, azulene, chamomile active ingredients and acetylsalicylic acid derivatives.

One preferred embodiment of the cosmetic preparations is toothpastes in the form of an aqueous, pasty dispersion, containing polishing agents, humectants, viscosity regulators and optionally further customary components, and also the mixture of menthofuran and menthol compounds in amounts of 0.5% to 2% by weight.

To improve the flow behavior, in addition, hydrotropic agents, for example ethanol, isopropyl alcohol or polyols can be used; these substances correspond substantially to the carriers described at the outset. Useful polyols here preferably have 2 to 15 carbon atoms and at least two hydroxyl groups. The polyols can contain even further functional groups, in particular amino groups, and/or be modified by nitrogen. Typical examples are glycerol;

alkylene glycols, for example ethylene glycol, diethylene glycol, propylene glycol, butylene glycol, hexylene glycol and also polyethylene glycols having an average molecular weight from 100 to 1000 daltons;

technical oligoglycerol mixtures having a degree of self-condensation of 1.5 to 10 such as technical diglycerol mixtures having a diglycerol content of 40 to 50% by weight;

methylol compounds such as, in particular, trimethylolethane, trimethylolpropane, trimethylolbutane, pentaerythritol and dipentaerythritol;

lower alkylglucosides, in particular those having 1 to 8 carbon atoms in the alkyl radical, for example methyl- and butylglucoside;

sugar alcohols having 5 to 12 carbon atoms, for example sorbitol or mannitol, sugars having 5 to 12 carbon atoms, for example glucose or sucrose;

amino sugars, for example glutamine;

dialcoholamines, such as diethanolamine or 2-amino-1,3-propanediol.

Suitable preservatives are, for example, phenoxyethanol, formaldehyde solution, parabens, pentanediol or sorbic acid, and also the silver complexes known under the name Surfacine® and the further classes of substances listed in annex 6, part A and B of the Kosmetikverordnung [German Cosmetics Act].

Perfume oils include mixtures of natural and synthetic odor substances. Natural odorants are extracts of blossoms (lily, lavender, roses, jasmine, neroli, ylang-ylang), stalks and leaves (geranium, patchouli, petitgrain), fruits (aniseed, coriander, cumin, juniper), fruit skins (bergamot, lemon, oranges), roots (mace, angelica, celeriac, cardamom, costus, iris, calmus), woods (pine, sandal, guaiac, cedar, rosewood), herbs and grasses (tarragon, lemon grass, sage, thyme), needles and twigs (spruce, fir, pine, mountain pine), resins and balsams (galbanum, elemi, benzoin, myrrh, olibanum, opoponax). In addition, animal raw materials come into consideration, for example civet and castoreum. Typical synthetic odorant compounds are products of the type of esters, ethers, aldehydes, ketones, alcohols and hydrocarbons. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxy-acetaldehyde, cyclamen aldehyde, hydroxycitronellal, lilial and bourgeonal, the ketones include, for example, the ionones, α-isomethylionone and methyl cedryl ketone, the alcohols include anethole, citronellol, eugenol, isoeugenol, geraniol, linalool, phenylethyl alcohol and terpineol, the hydrocarbons include chiefly the terpenes and balsams. However, preference is given to using mixtures of various odorants which together generate a pleasant fragrance note. Also essential oils of lower volatility which are generally used as aroma components are suitable as perfume oils, e.g. salvia oil, chamomile oil, clove oil, melissa oil, mint oil, cinnamon leaf oil, linden blossom oil, juniper berry oil, vetiver oil, olibanum oil, galbanum oil, labolanum oil and lavender oil. Preferably, bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, Ambroxan, indole, hedione, sandelice, lemon oil, mandarin oil, orange oil, allyl amyl glycolate, cyclovertal, lavender oil, Salvia sclarea oil, O-damascone, geranium bourbon oil, cyclohexyl salicylate, Vertofix Coeur, Iso E Super, Fixolide NP, evernyl, iraldein gamma, phenylacetic acid, geranyl acetate, benzyl acetate, rose oxide, romilllate, irotyl and floramate are used alone or in mixtures.

Useful aromas include, for example, peppermint oil, spearmint oil, aniseed oil, star anise oil, caraway oil, eucalyptus oil, fennel oil, lemon oil, wintergreen oil, clove oil, menthol and the like Hydrotropes In order to improve the flow behavior, hydrotropes, for example ethanol, isopropyl alcohol, or polyols, can also be used; these substances largely correspond to the carriers described at the beginning. Useful polyols here preferably have 2 to 15 carbon atoms and at least two hydroxyl groups. The polyols may contain further functional groups, in particular amino groups, or be modified with nitrogen. Typical examples are glycerol;

alkylene glycols, for example ethylene glycol, diethylene glycol, propylene glycol, butylene glycol, hexylene glycol, and polyethylene glycols having an average molecular weight of 100 to 1000 daltons;

commercial oligoglycerol mixtures having an inherent degree of condensation of 1.5 to 10, for example commercial diglycerol mixtures having a diglycerol content of 40% to 50% by weight;

methylol compounds, such as, in particular, trimethylolethane, trimethylolpropane, trimethylol butane, pentaerythritol and dipentaerythritol;

lower alkyl glucosides, especially those having 1 to 8 carbon atoms in the alkyl moiety, for example methyl and butyl glucoside;

sugar alcohols having 5 to 12 carbon atoms, for example sorbitol or mannitol;

sugars having 5 to 12 carbon atoms, for example glucose or sucrose;

amino sugars, for example glutamine;

dialcohol amines, such as diethanolamine or 2-amino-1,3-propanediol.

Preservatives

Suitable preservatives are, for example, phenoxyethanol, formaldehyde solution, parabens, pentanediol or sorbic acid, and the silver complexes known by the Surfacine® name and the further substance classes listed in Annex 6, Parts A and B of the Kosmetikverordnung.

Perfume Oils, Aromas, Aroma Substances, Fragrances

Fragrances and perfume oils used with preference are not subject to any restrictions at all. Hence as fragrances it is possible to use individual odorant compounds, either synthetic or natural compounds of the class of esters, ethers, aldehydes, ketones, alcohols, hydrocarbons, acids, carbonic esters, aromatic hydrocarbons, aliphatic hydrocarbons, saturated and/or unsaturated hydrocarbons, and mixtures thereof. Fragrance aldehydes or fragrance ketones used may be all customary fragrance aldehydes and fragrance ketones which are typically employed in order to bring about a pleasant fragrance sensation. Suitable fragrance aldehydes and fragrance ketones are common knowledge to the skilled person. The fragrance ketones may encompass all ketones which are able to impart a desired fragrance or a sensation of freshness. Mixtures of different ketones may also be used. For example, the ketone may be selected from the group consisting of buccoxime, isojasmone, methyl beta-naphthyl ketone, musk indanone, Tonalid/musk plus, alpha-damascone, beta-damascone, delta-damascone, isodamascone, damascenone, damarose, methyl dihydrojasmonate, menthone, carvone, camphor, fenchone, alpha-ionone, Neta-ionone, dihydro-beta-ionone, gamma-methylionone (so-called), fleuramone, dihydrojasmone, cisjasmone, Iso-E-Super, methyl cedrenyl ketone or methyl-cedrylone, acetophenone, methylacetophenone, para-methoxyacetophenone, methyl beta-naphthyl ketone, benzylacetone, benzophenone, para-hydroxyphenylbutanone, celery ketone or livescone, 6-isopropyldecahydro-2-naphthone, dimethyl-octenone, Freskomenthe, 4-(1-ethoxyvinyl)-3,3,5,5-tetramethylcyclohexa none, methylheptenone, 2-(2-(4-methyl-3-cyclohexen-1-yl)propyl)cyclopentanone, 1-(p-menthen-6(2)-yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)-indanone, 4-damascol, dulcinyl or cassione, gelsone, hexalone, isocyclemone E, methyl-cyclocitrone, methyl-lavender ketone, orivone, para-tert-butylcyclohexanone, verdone, delphone, muscone, neobutenone, plicatone, veloutone, 2,4,4,7-tetra methyloct-6-en-3-one, tetramerane, hedione and mixtures thereof. The ketones may preferably be selected from alpha-damascone, delta-damascone, isodamascone, carvone, gamma-methyl-ionone, Iso-E-Super, 2,4,4,7-tetra methyloct-6-en-3-one, benzylacetone, beta-damascone, damascenone, methyl dihydrojasmonate, methylcedrylone, hedione and mixtures thereof.

Suitable fragrance aldehydes may be any desired aldehydes which, in the same way as for the fragrance ketones, impart a desired odor or a sensation of freshness. Again they may be individual aldehydes or aldehyde mixtures. Suitable aldehydes are, for example, melonal, triplal, ligustral, adoxal, anisaldehyde, cymal, ethylvanillin, florhydral, floralozone, helional, heliotropin, hydroxycitronellal, koavone, lauryl aldehyde, canthoxal, lyral, lilial, adoxal, anisaldehyde, cumal methylnonylacetaldehyde, citronellal, citronellyloxy-acetaldehyde, cyclamen aldehyde, bourgeonal, p,t-bucinal, phenylacetaldehyde, undecylenealdehyde, vanillin; 2,6,10-trimethyl-9-undecenal, 3-dodecen-1-al, alpha-n-amylcinnamaldehyde, 4-methoxybenzaldehyde, benzaldehyde, 3-(4-tert-butylphenyl)propanal, 2-methyl-3-(para-methoxyphenyl)propanal, 2-methyl-4-(2,6,6-trimethyl-2(1)-cyclohexen-1-yl)butanal, 3-phenyl-2-propenal, cis/trans-3,7-dimethyl-2,6-octadien-1-al, 3,7-dimethyl-6-octen-1-al, [(3,7-dimethyl-6-octenyl)oxy]acetaldehyde, 4-isopropylbenzyl aldehyde, 1,2,3,4,5,6,7,8-octahydro-8,8-dimethyl-2-naphthaldehyde, 2,4-dimethyl-3-cyclohexene-1-carboxyaldehyde, 2-methyl-3-(isopropylphenyl)propanal, decyl aldehyde, 2,6-dimethyl-5-heptenal; 4-(tricyclo[5.2.1.0$^{1,6}$]decylidene-8)-butanal; octahydro-4,7-methano-1H-indenecarboxaldehyde; 3-ethoxy-4-hydroxybenzaldehyde, para-ethyl-alpha,alpha-dimethylhydrocinnamaldehyde, alpha-methyl-3,4-(methylenedioxy)-hydrocinnamaldehyde, 3,4-methylenedioxybenzaldehyde, alpha-n-hexylcinnamaldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexene-3-carboxaldehyde, 4-(4-hydroxy-4-methylpentyl)-3-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, 3-(4-ethylphenyl)-2,2-dimethylpropanal, 3-(4-methoxyphenyl)-2-methylpropanal, methylnonylacetaldehyde, 2-phenylpropan-1-al, 3-phenylprop-2-en-1-al, 3-phenyl-2-pentylprop-2-en-1-al, 3-phenyl-2-hexylprop-2-enal, 3-(4-isopropylphenyl)-2-methylpropan-1-al, 3-(4-ethylphenyl)-2,2-dimethylpropan-1-al, 3-(4-tert-butylphenyl)-2-methylpropanal, 3-(3,4-methylenedioxyphenyl)-2-methylpropan-1-al, 3-(4-ethylphenyl)-2,2-dimethylpropanal, 3-(3-isopropylphenyl)butan-1-al, 2,6-dimethylhept-5-en-1-al, dihydrocinnamaldehyde, 1-methyl-4-(4-methyl-3-pentenyl)-3-cyclohexene-1-carboxaldehyde, 5- or 6-methoxyhexahydro-4,7-methanoindane-1- or -2-carboxyaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexenecarboxaldehyde, 7-hydroxy-3,7-dimethyloctanal; trans-4-decenal, 2,6-nonadienal, para-tolylacetaldehyde; 4-methylphenylacetaldehyde, 2-methyl-4-(2,6,6-trimethyl-1-cyclohexen-1-yl)-2-butenal, ortho-methoxycinnamaldehyde, 3,5,6-trimethyl-3-cyclohexenecarboxaldehyde, 3,7-dimethyl-2-methylene-6-octenal, phenoxyacetaldehyde; 5,9-dimethyl-4,8-decadienal, peony aldehyde (6,10-dimethyl-3-oxa-5,9-undecadien-1-al), hexahydro-4,7-methanoindane-1-carboxaldehyde, octanal, 2-methyloctanal, alpha-methyl-4-(1-methylethyl)benzeneacetaldehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propylbicyclo[2.2.1]hept-5-ene-2-carbaldehyde, 9-decenal, 3-methyl-5-phenyl-1-pentanal, methylnonylacetaldehyde, 1-p-menthene-q-carboxaldehyde, citral or mixtures thereof, lilial citral, 1-decanal, n-undecanal, n-dodecanal, florhydral, 2,4-dimethyl-3-cyclohexene-1-carboxaldehyde, 4-methoxybenzaldehyde, 3-methoxy-4-hydroxybenzaldehyde, 3-ethoxy-4-hydroxybenzaldehyde, 3,4-methylenedioxybenzaldehyde and 3,4-dimethoxybenzaldehyde and mixtures thereof. As observed by way of example above, the fragrance aldehydes and fragrance ketones may have an aliphatic, cycloaliphatic, aromatic, ethylenically unsaturated structure or a combination of these structures. There may also be further heteroatoms or polycyclic structures present. The structures may have suitable substituents such as hydroxyl groups or amino groups. For further suitable fragrances, selected from aldehydes and ketones, reference is made to Steffen Arctander, published 1960 and 1969 respectively, reprinted 2000 ISBN: Aroma Chemicals Vol. 1: 0-931710-37-5, Aroma Chemicals Vol. 2: 0-931710-38-3.

Suitable odorant compounds of the ester type are, for example, benzyl acetate, phenoxyethyl isobutyrate, p-tert-butylcyclohexyl acetate, linalyl acetate, dimethylbenzyl carbinyl acetate (DM BCA), phenylethyl acetate, benzyl acetate, ethyl methyl phenylglycinate, allyl cyclohexylpropionate, styrallyl propionate, benzyl salicylate, cyclohexyl salicylate, floramate, melusate and jasmacyclate. Odorant compounds of the hydrocarbon type are, for example, terpenes such as limonene and pinene. Suitable fragrances of the ether type are, for example, benzyl ethyl ether and ambroxane. Suitable fragrance alcohols are, for example, 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 1-octen-3-ol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, alpha-methylbenzyl alcohol, alpha-terpineol, amyl salicylate, benzyl alcohol, benzyl salicylate, beta-terpineol, butyl salicylate, citronellol, cyclohexyl salicylate, decanol, dihydromyrcenol, dimethylbenzyl carbinol, dimethylheptanol, dimethyloctanol, ethyl Salicylate, ethylvanilin, anethol, eugenol, geraniol, heptanol, hexyl salicylate, isoborneol, isoeugenol, isopulegol, linalool, menthol, myrtenol, n-hexanol, nerol, nonanol, octanol, para-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol; if two or more fragrance alcohols are present, they may be selected independently of one another.

Fragrances and perfume oils may also be natural odorant mixtures, such as those obtainable from plant sources, examples being pine, citrus, jasmine, patchouli, rose or ylang-ylang oil. Likewise suitable are clary sage oil, camomile oil, clove oil, balm oil, mint oil, cinnamon leaf oil, lime blossom oil, juniper berry oil, vetiver oil, olibanum oil, galbanum oil and labdanum oil, and also orange blossom oil, neroli oil, orange peel oil and sandalwood oil. Essential oils such as angelica root oil, aniseed oil, arnica blossom oil, basil oil, bay oil, champaca flower oil, silver fir oil, silver fir cone oil, elemi oil, eucalyptus oil, fennel oil, pine needle oil, galbanum oil, geranium oil, gingergrass oil, guaiac wood oil, gurjan balsam oil, helichrysum oil, ho oil, ginger oil, iris oil, cajeput oil, sweet flag oil, camomile oil, camphor oil, cananga oil, cardamom oil, cassia oil, pine needle oil, copaiba balsam oil, coriander oil, spearmint oil, caraway oil, cumin oil, lavender oil, lemongrass oil, lime oil, mandarin oil, melissa oil, amber seed oil, myrrh oil, clove oil, neroli oil, niaouli oil, olibanum oil, oregano oil, palmarosa oil, patchouli oil, peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, citrus oil and cypress oil.

Likewise suitable as fragrance are what are called fragrance precursors (pro-drugs). This class of compounds comprises compounds which release a desired odor molecule and/or fragrance molecule through the breaking of a chemical bond, by hydrolysis, for example. To form a fragrance precursor, typically, a desired fragrance raw material is joined chemically to a carrier, preferably a carrier of low or moderate volatility. The combination results in a less volatile and more strongly hydrophobic fragrance precursor, with better attachment to materials. The fragrance is released subsequently by breaking of the bond between the fragrance raw material and the carrier, as a result of the change in pH, for example (through perspiration during wear, for example), atmospheric humidity, heat and/or sunlight during storage or during drying on a washing line.

The fragrance raw material for use in fragrance precursors typically comprises saturated or unsaturated volatile compounds containing an alcohol, an aldehyde and/or a ketone group. The fragrance raw materials that are useful herein include any pleasingly odorous substances or mixtures of substances which have already been described above.

Particularly advantageous fragrance precursors which can be used conform to the formula (III)

R—C(OR$^1$)(OR$^2$)—OR$^3$ (III)

in which R is hydrogen, linear $C_1$-$C_8$ alkyl, branched $C_3$-$C_{20}$ alkyl, cyclic $C_3$-$C_{20}$ alkyl, branched cyclic $C_5$-$C_{20}$ alkyl, linear $C_5$-$C_{20}$ alkenyl, branched $C_6$-$C_{20}$ alkenyl, cyclic $C_5$-$C_{20}$ alkenyl, branched cyclic $C_5$-$C_{20}$ alkenyl, substituted or unsubstituted $C_6$-$C_{20}$ aryl and mixtures thereof; $R^1$, $R^2$ and $R^3$ independently are linear, branched or substituted $C_1$-$C_{20}$ alkyl; linear, branched or substituted $C_2$-$C_{20}$ alkenyl; substituted or unsubstituted, cyclic $C_3$-$C_{20}$ alkyl; substituted or unsubstituted $C_5$-$C_{20}$ aryl, substituted or unsubstituted $C_2$-$C_{40}$ alkyleneoxy; substituted or unsubstituted $C_3$-$C_{40}$ alkyleneoxyalkyl; substituted or unsubstituted $C_6$-$C_{40}$ alkylenearyl; substituted or unsubstituted $C_5$-$C_{32}$ aryloxy; substituted or unsubstituted $C_6$-$C_{40}$ alkyleneoxyaryl; $C_6$-$C_{40}$ oxyalkylenearyl and mixtures thereof. The use of such substances, especially in (preferably water-insoluble) microcapsules, corresponds to one preferred embodiment of the invention.

Further particularly advantageous fragrance precursors which can be used are acetals or ketals, preferably conforming to the formula (IV)

R—C(R$^1$)(OR$^3$)—OR$^2$ (IV)

in which R is linear $C_1$-$C_{20}$ alkyl, branched $C_3$-$C_{20}$ alkyl, cyclic $C_5$-$C_{20}$ alkyl, branched cyclic $C_5$-$C_{20}$ alkyl, linear $C_2$-$C_{20}$ alkenyl, branched $C_3$-$C_{20}$ alkenyl, cyclic $C_5$-$C_{20}$ alkenyl, branched cyclic $C_6$-$C_{20}$ alkenyl, substituted or unsubstituted $C_6$-$C_{20}$ aryl and mixtures thereof; $R^1$ is hydrogen or R; $R^2$ and $R^3$ each independently of one another are selected from the group consisting of linear $C_1$-$C_{20}$ alkyl, branched $C_3$-$C_{20}$ alkyl, cyclic $C_3$-$C_{20}$ alkyl, branched cyclic $C_6$-$C_{20}$ alkyl, linear $C_5$-$C_{20}$ alkenyl, branched $C_5$-$C_{20}$ alkenyl, cyclic $C_6$-$C_{20}$ alkenyl, branched cyclic $C_5$-$C_{20}$ alkenyl, $C_6$-$C_{20}$ aryl, substituted $C_7$-$C_{20}$ aryl and mixtures thereof. The use of such substances, especially in (preferably water-insoluble) microcapsules, corresponds to one preferred embodiment of the invention.

Further particularly advantageous fragrance precursors which can be used conform to the formula (V)

R$^4$O—C(OR$^1$)(OR$^3$)—OR$^2$ (V)

in which $R^1$, $R^2$, $R^3$ and $R^4$ independently of one another are linear, branched or substituted $C_1$-$C_{20}$ alkyl; linear, branched or substituted $C_2$-$C_{20}$ alkenyl; substituted or unsubstituted, cyclic $C_5$-$C_{20}$ alkyl; substituted or unsubstituted $C_6$-$C_{20}$ aryl, substituted or unsubstituted $C_2$-$C_{40}$ alkyleneoxy; substituted or unsubstituted $C_3$-$C_{40}$ alkyleneoxyalkyl; substituted or unsubstituted $C_6$-$C_{40}$ alkylenearyl; substituted or unsubstituted $C_6$-$C_{32}$ aryloxy; substituted or unsubstituted $C_6$-$C_{40}$ alkyleneoxyaryl; $C_6$-$C_{40}$ oxyalkylenearyl; and mixtures thereof. The use of such substances, especially in (preferably water-insoluble) microcapsules, corresponds to one preferred embodiment of the invention.

It is particularly preferable for the odorants used to comprise silicic ester mixtures. Silicic esters are described for example by the formula (V)

$$R-(-O-Si(OR)_2-)_n-OR \qquad (V)$$

where R independently at each occurrence is selected from the group containing H, the straight-chain or branched, saturated or unsaturated, substituted or unsubstituted $C_1$-$C_6$ hydrocarbon radicals and the fragrance alcohol radicals and/or biocide alcohol radicals, and m adopts values from the range from 1 to 20 and n adopts values from the range from 2 to 100. The silicic esters of the formulae preferably comprise at least one fragrance alcohol residue and/or biocide alcohol residue.

The silicic ester mixtures may be used in encapsulated form, but also in unencapsulated form. The effect of the presence of silicic ester mixtures is often that the fragrance impression achievable, both with regard to pleasure and intensity, can be improved still further. The fragrance impression is not just qualitatively better, i.e. with regard to pleasure, but also lasts longer.

The silicic ester mixtures may also be present in the microcapsules. If the silicic ester mixtures in the microcapsules make up preferably at least 2% by weight of the total amount of encapsulated odorant, % by weight based on the amount of encapsulated odorants, this is a preferred embodiment of the invention, which brings about a further improvement in the desired pleasing odor effect after drying.

Particularly suitable fragrance precursors are reaction products of compounds comprising at least one primary and/or secondary amine group, for example an amino-functional polymer, especially an amino-functional silicone, and a fragrance constituent selected from ketone, aldehyde and mixtures thereof. Useful aromas include, for example, peppermint oil, spearmint oil, aniseed oil, star anise oil, caraway oil, eucalyptus oil, fennel oil, lemon oil, wintergreen oil, clove oil, menthol and the like.

Aroma substances include, for example: acetophenone, allyl caproate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl caproate, butylidene phthalide, carvone, camphene, caryophyllene, cineole, cinnamyl acetate, citral, citronellol, citronellal, citronellyl acetate, cyclohexyl acetate, cymene, damascone, decalactone, dihydrocoumarin, dimethyl anthranilate, dimethyl anthranilate, dodecalactone, ethoxyethyl acetate, ethylbutyric acid, ethyl butyrate, ethyl caprate, ethyl caproate, ethyl crotonate, ethylfuraneol, ethylguaiacol, ethyl isobutyrate, ethyl isovalerate, ethyl lactate, ethyl methylbutyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamylisovalerate, isobutyl butyrate, isobutyraldehyde, isoeugenol methyl ether, isopropyl methylthiazole, lauric acid, laevulinic acid, linalool, linalool oxide, linalyl acetate, menthol, menthofuran, methyl anthranilate, methylbutanol, methylbutyric acid, 2-methylbutyl acetate, methyl caproate, methyl cinnamate, 5-methylfurfural, 3,2,2-methylcyclopentenolone, 6,5,2-methylheptenone, methyl dihydrojasmonate, methyl jasmonate, 2-methylmethylbutyrate, 2-methyl-2-pentenolic acid, methyl thiobutyrate, 3,1-methylthiohexanol, 3-methylthiohexyl acetate, nerol, neryl acetate, trans,trans-2,4-nonadienal, 2,4-nonadienol, 2,6-nonadienol, 2,4-nonadienol, nootkatone, delta-octalactone, gamma-octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerate, piperonal, propionaldehyde, propyl butyrate, pulegone, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3(2H)-furanone and derivatives thereof (here preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (here preferably ethylmaltol), coumarin and coumarin derivatives, gamma-lactones (here preferably gamma-undecalactone, gamma-nonalactone, gamma-decalactone), delta-lactones (here preferably 4-methyldeltadecalactone, massoialactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, isoamyl acetate, ethyl butyrate, n-butyl butyrate, isoamyl butyrate, ethyl 3-methylbutyrate, ethyl n-hexanoate, allyl n-hexanoate, n-butyl n-hexanoate, ethyl n-octanoate, ethyl-3-methyl-3-phenylglycidate, ethyl 2-trans-4-cis-decadienoate, 4-(p-hydroxyphenyl)-2-butanone, 1,1-dimethoxy-2,2,5-tri-methyl-4-hexane, 2,6-dimethyl-5-hepten-1-al and phenylacetaldehyde, 2-methyl-3-(methylthio)furan, 2-methyl-3-furanthiol, bis(2-methyl-3-furyl)disulfide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamyl alcohol, methyl salicylate, isopulegol and also (not explicitly stated here) stereoisomers, enantiomers, positional isomers, diastereomers, cis/trans isomers or epimers of these substances.

Preference is given to using mixtures of various fragrances (from the different abovementioned fragrance classes) which together generate a pleasing fragrance note. In this case, the total amount of the at least one fragrance is the amount of all fragrances in the mixture together based on the total amount of the composition.

Dyes

Dyes used may be the substances that are suitable and approved for cosmetic purposes, as compiled, for example, in the publication "Kosmetische Farbemittel" [Cosmetic Colorants] issued by the Farbstoffkommission [Dyes Commission] of the Deutsche Forschungsgemeinschaft [German Research Foundation], Verlag Chemie, Weinheim, 1984, p. 81-106. Examples are cochineal red A (C.I. 16255), patent blue V (C.I.42051), indigotin (C.I.73015), chlorophyllin (C.I.75810), quinoline yellow (C.I.47005), titanium dioxide (C.I.77891), indanthrene blue RS (C.I. 69800) and rose madder (C.I.58000). Luminol may also be present as luminescent dye. These dyes are typically used in concentrations of 0.001% to 0.1% by weight, based on the overall mixture.

The proportion by weight of the auxiliaries and additives may be 1% to 50%, preferably 5% to 40%, by weight—based on the compositions. The compositions can be produced by customary low- or high-temperature processes; preference is given to working by the phase inversion temperature method.

Likewise suitable are the known approved food dyes:

| | | |
|---|---|---|
| Allura red AC | E 129 | red |
| Aluminum | E 173 | silvery gray |
| Amaranth | E 123 | red |
| Anthocyanines | E 163 | violet, blue |
| Azorubine | E 122 | red |
| Betanin | E 162 | red |
| Brown FK | E 154 | yellow-brown |
| Brown HT | E 155 | red-brown |
| Brilliant blue FCF | E 133 | blue |
| Brilliant black BN | E 151 | violet, brown, black |
| Calcium carbonate | E 170 | |
| Canthaxanthin | E 161 | g |
| Carotene | E 160 | a |
| * Annatto (norbixin) | E 160 | b |
| * Capsanthin | E 160 | c |
| * Lycopene | E 160 | d |
| * 8'-Apo-β-caroten-8'-al | E 160 | e |
| * Ethyl 8'-apo-β-caroten-8'-oate | E 160 | f |
| Quinoline yellow | E 104 | |
| Chlorophyll | E 140 | green |
| Cochineal red A | E 124 | |
| Curcumin | E 100 | |
| Iron oxide | E 172 | |
| Erythrosin | E 127 | |
| Yellow orange S | E 110 | |
| Gold | E 175 | |
| Green S | E 142 | |
| Indigotin | E 132 | |
| Cochineal | E 120 | |
| Copper-containing complexes of the chlorophylls and chlorophyllins | E 141 | |
| Lactoflavin | E 101 | |
| Litholrubin BK | E 180 | |
| Lutein | E 161 | b |
| Patent blue V | E 131 | |
| Plant charcoal | E 153 | |
| Riboflavin (vitamin B2) | E 101 | |
| * Riboflavin-5-phosphate | E 101 | a |
| Safflower | | cherry red to brown-yellow |
| Silver | E 174 | |
| Tartrazine | E 102 | lemon yellow |
| Titanium dioxide | E 171 | |
| Caramel color | E 150 | a |
| *Sulfite liquor caramel color | E 150 | b |
| *Ammonia caramel color | E 150 | c |
| *Ammonium sulfite caramel color | E 150 | d |
| Zeaxanthin | E 161 | h |

Abbreviations Used

Dipropylene glycol (DPG), diethyl phthalate (DEP), triethyl citrate (TEC), isopropyl myristate (IPM); nat.=natural;

For elucidations of the product names of the odorants see, for example, S. Arctander, Perfume and Flavor Materials, Vol. I and II, Montclair, N.J., 1969, self-published or H. Surburg, J. Panten, "Common Fragrance and Flavor Materials", 5th. ed., Wiley-VCH, Weinheim 2006.

EXAMPLES

Example 1

General Preparation Method for a Compound of the Formula (I)

Preparation Example:
1-cyclopent-2-en-1-ylpropan-2-one

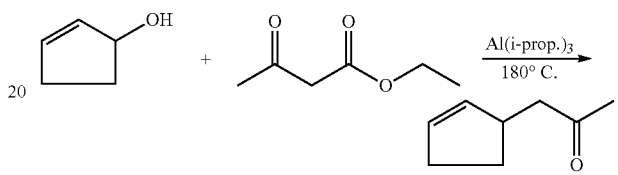

A 100 ml three-neck flask with magnetic stirrer, contact thermometer, dropping funnel, 5 cm Vigreux column and distillation apparatus is initially charged with 69 mg (0.34 mmol) of aluminum triisopropoxide and 4.6 g (0.035 mol) of ethyl acetoacetate and heated up to 180° C. At this temperature, a solution of 12.6 g (0.15 mol) of 2-cyclopentanol and 21 g (0.16 mol) of ethyl acetoacetate is added dropwise within 2 h, with constant removal of distillate and evolution of carbon dioxide. The mixture is stirred at 180° C. for another 2 h. The residue (13 g) is distilled using a Kugelrohr (boiling range: 110° C./80-40 mbar). 8.1 g of distillate are obtained (GC: 84% product). 2.7 g of the distillate are subjected to preparative column treatment on 120 g of silica gel 60 with hexane/ethyl acetate (Büchi PrepChrom C-700, column: 120 g (SepaCore)). Yield: 1.5 g (GC: 99% product).

Example 2

List of Compounds of the General Formula (I) with Odor Descriptions and MS Data

Methyl 2-cyclopent-2-en-1-ylacelale (compound II)

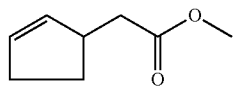

GCMS: m/z (%)=140(11), 109(15), 108(20), 80(33), 79(31), 74(43), 67(100), 66(25), 43(16), 41(23), 39(20)
Odor profile: fruity in the strawberry direction Ethyl 2-cyclopent-2-en-1-ylacetate (compound III)

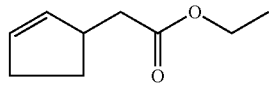

GCMS: m/z (%)=154(31), 109(25), 108(27), 88(39), 83(36), 80(47), 79(64), 67(100), 66(28), 41(23)

Odor profile: sweet, fruity, green, in the direction of pear, pineapple, apricot and kiwi Propyl 2-cyclopent-2-en-1-ylacetate (compound IV)

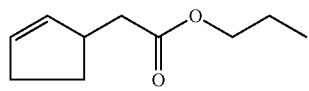

GCMS: m/z (%)=168(6), 109(30), 108(27), 107(20), 83(26), 80(32), 79(44), 67(100), 66(31), 61(22), 41(28)

Odor profile: sweet, fruity, green, fatty, in the pineapple direction

Isopropyl 2-cyclopent-2-en-1-yl acetate (compound V)

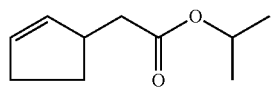

GCMS: m/z (%)=168(1), 126(16), 125(15), 109(21), 108(29), 80(15), 79(26), 67(100), 66(34), 43(17), 41(17)

Odor profile: sweet, fruity, bergamot and violet

Allyl 2-cyclopent-2-en-1-ylacetate (compound VI)

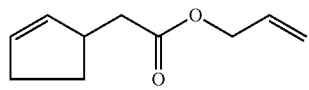

GCMS: m/z (%)=125(56), 107(42), 83(62), 80(18), 79(100), 77(12), 67(82), 66(14), 41(56), 39(29)

Odor: sweet, fruity, green, in the pineapple direction

Isopentyl 2-cyclopent-2-en-1-ylacetate (compound VII)

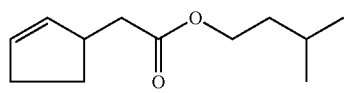

GCMS: m/z (%)=196(4), 80(23), 79(33), 71(51), 70(27), 67(81), 66(23), 43(100), 41(52), 39(25), 27(22)

Odor profile: sweet, fruity, green, in the apple and pear direction

Cyclopentyl 2-cyclopent-2-en-1-ylacetate (compound VIII)

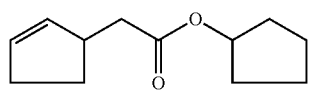 [SMILES: O=C(CC1C=CCC1)OC1CCCC1]

GCMS: m/z (%)=126(18), 109(21), 108(37), 80(13), 79(13), 69(9), 68(9), 67(100), 66(25), 41(22)

Odor profile: sweet, fruity, in the pineapple direction

[(E)-But-2-enyl]2-cyclopent-2-en-1-ylacetate (compound IX)

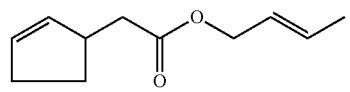

GCMS: m/z (%)=125(65), 108(17), 107(41), 83(51), 79(76), 67(100), 66(26), 55(49), 41(22), 39(22)

Odor profile: sweet, mushroomy, fruity, in the pineapple direction

Cyclopropylmethyl 2-cyclopent-2-en-1-ylacetate (compound X)

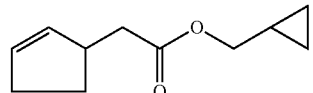

GCMS: m/z (%)=125(33), 107(38), 83(35), 80(19), 79(56), 67(80), 55(100), 41(17), 39(17), 29(21)

Odor profile: sweet, mushroomy, fruity, in the pineapple direction 1,2-Dimethylpropyl 7-cyclopent-2-en-1-ylacetate (compound XI)

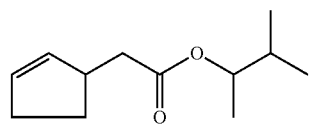

GCMS: m/z (%)=126(14), 109(57), 108(25), 79(13), 71(43), 70(24), 67(100), 66(19), 43(42), 41(15)

Odor profile: sweet, green, fruity, in the pineapple direction

Ethyl 2-(cyclopenten-1-yl) acetate (compound XII)

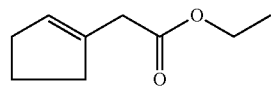

GCMS: (%)=154(36), 125(6), 108(39), 88(9), 83(36), 81(100), 67(45), 53(21), 41(22)

Odor profile: sweet, fresh, fruity, in the apple direction

Methyl 2-cyclopentylideneacetate (compound XIII)

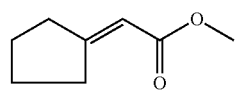

GCMS: m/z (%)=140(100), 125(7), 109(66), 81(42), 74(26), 67(31), 53(25), 41(28)

Odor profile: sweet, green, fruity, in the banana direction, floral like ylang and honey-like Methyl 2-cyclopentylacetate (compound XIV)

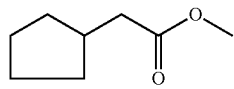

GCMS: m/z (%)=142(1), 111(11), 99(10), 83(11), 75(28), 74(100), 67(11), 59(10), 55(22), 43(23), 41(20)

Odor profile: sweet, fruity, in the valerate direction

Propyl 2-cyclopentylacetate (compound XV)

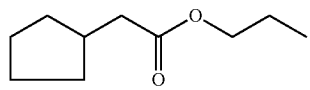

GCMS: m/z (%)=129(43), 111(56), 102(17), 83(48), 67(21), 61(100), 60(48), 55(34), 43(24), 41(35)

Odor profile: sweet, fruity, in the banana direction

Allyl 2-cyclopentylacetate (compound XVI)

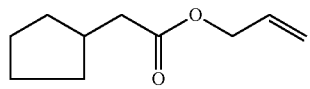

GCMS: m/z (%)=168(2), 111(50), 100(36), 83(100), 82(17), 67(45), 55(76), 54(19), 43(24), 41(87), 39(24)

Odnr arofile: sweet, green, fruity, in the pineapple direction

Isopropyl 2-cyclopentylacetate (compound XVII)

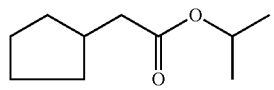

GCMS: m/z (%)=129(34), 111(63), 102(48), 83(67), 68(32), 61(62), 60(100), 55(43), 43(69), 41(48)

Odor: sweet, fruity, in the banana direction, floral, rosy

[(E)-But-2-enyl]2-cyclopentylacetate (compound XVIII)

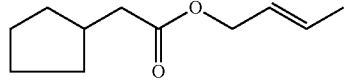

GCMS: m/z (%)=182(4), 111(50), 109(12), 83(77), 67(23), 55(100), 54(14), 41(19), 39(13), 29(16), 27(10)

Odor profile: sweet, fruity, in the pineapple direction, citrus-like

3-Methylbut-2-enyl 2-cyclopent-2-en-1-ylacetate (compound XIX)

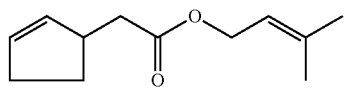

GCMS: m/z (%)=126(23), 125(31), 108(29), 83(22), 79(32), 69(79), 68(39), 67(100), 66(22), 41(62)

Odor profile: sweet, fruity

Ethyl 2-cyclopentylacetate (compound XX)

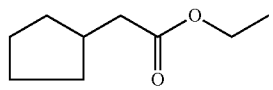

GCMS: m/z (%)=156(1), 111(26), 89(23), 88(100), 83(30), 70(33), 61(27), 60(28), 55(29), 41(33), 29(22)

Odor profile: sweet, fruity, in the apple and strawberry direction

1-Cyclopent-2-en-1-ylpropan-2-one (compound XXII)

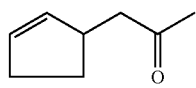

GCMS: m/z (%)=124(34), 109(27), 81(20), 79(21), 67(72), 66(100), 65(11), 43(68), 41(18), 39(18)

Odor profile: green, fruity, nutty

1-Cyclopent-2-en-1-ylhexan-2-one (compound XXII)

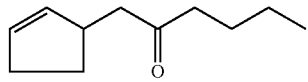

GCMS: m/z (%)=166(9), 109(100), 85(15), 81(17), 79(19), 67(93), 57(41), 41(53), 29(31), 27(20)
Odor profile: green, fruity 1-Cyclopent-2-en-1-ylpent-4-en-2-one (compound XXIII)

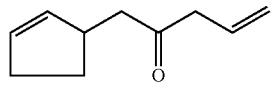

GCMS: m/z (%)=150(1), 109(42), 81(7), 79(8), 68(6), 67(100), 66(5), 65(6), 53(5), 41(19), 39(10)
Odor profile: green, fruity (E)-1-Cyclopent-2-en-1-ylpent-3-en-2-one (compound XXIV)

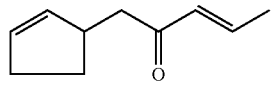

GCMS: m/z (%)=150(5), 122(16), 107(16), 84(42), 80(26), 79(18), 69(100), 67(43), 66(16), 41(48), 39(22)
Odor profile: green, fruity, somewhat eugenol-like (Z)-1-Cyclopent-2-en-1-ylpent-3-en-2-one (compound XXV)

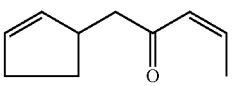

GCMS: m/z (%)=150(5), 122(16), 107(16), 84(50), 80(27), 79(19), 69(100), 67(32), 66(15), 41(17), 39(23)
Odor profile: green, fruity, somewhat eugenol-like Example 3

Odor Description of Preferred Odorants After Addition of Compounds of the Formula (I) or (Ia)

| Odorants | Type | Compound of the formula (I) or (Ia) | Mass ratio of the odorant to the compound of the formula (I) or (Ia) (0.1% in DPG) | Odor description by comparison with the odor of the pure odorant |
|---|---|---|---|---|
| Cantryl (M = 149) | Nitrile | VI | 99:1.0 | Softer, more natural, more lively, spicier in the direction of thyme |
| Menthone (M = 154) | Ketone | XIX | 99:1.0 | The odorant loses its metallic note and seems more natural, sweeter with a sweet peppermint character |
| Peonile (M = 197) | Nitrile | I | 99:1.0 | Less industrial, fresh, natural salicyl-like flower note |
| Parmanyl (M = 153) | Nitrile | XIII | 99:1.0 | Less fatty, less metallic, more rounded, more natural, much more volume and impact |
| Tolylacetaldehyde (M = 134) | Aldehyde | VI | 100:1.0 | Less metallic, fresher, more natural, more rounded and sweeter in the almond direction |
| Phenylacetaldehyde (M = 120) | Aldehyde | XIX | 100:1.0 | Less greasy, less metallic, more rounded |
| Cyclogalbanate (M = 198) | Ester | I | 100:1.0 | Less metallic, more rounded, more natural |
| Frescomenthe (M = 154) | Ketone | XII | 100:1.0 | Less metallic, more rounded, more harmonic with natural effects |
| Isooctanone (M = 128) | Ketone | XIV | 100:1.0 | Less metallic, more rounded, more harmonic, fresher with Cognac effect |
| Ethyl cinnamate (M = 176) | Ester | XIV | 100:1.0 | Less metallic, more rounded, more harmonic, sweet, balsamic note |

Conclusion: The compounds of the formula (I) or (Ia) promote the natural lively effect in hereby, minty and green odorants.

Example 4

Perfume Oils P1-P5

TABLE 1

Perfume oil P1 (amounts in g)

| Ingredient | Formulation A | Formulation B |
|---|---|---|
| Aldehyde C11 MOA | 4 | 4 |
| Aldehyde C12 MNA | 1 | 1 |
| Limonenal | 6 | 6 |
| Magnolan | 50 | 50 |
| Mintonat | 50 | 50 |
| Dihydromyrcenol | 50 | 50 |
| Citral 95 | 5 | 5 |
| Mandaril | 1 | 1 |
| Citronitrile | 50 | 50 |
| Agrunitrile | 50 | 50 |
| Citronella Oil | 4 | 4 |
| Citrylal | 30 | 30 |
| Orange Oil Terpenes | 180 | 180 |
| Oxanthia 50% 10% | 6 | 6 |
| Phellandrene alpha L Natural | 140 | 140 |
| Eucalyptol Nat. | 17 | 17 |
| Carvone L | 17 | 17 |
| Thymol Cryst. | 4 | 4 |
| Basil Oil GRD Vert Type Linalool | 1 | 1 |
| Borneol L | 6 | 6 |
| Ethyl butyrate | 4 | 4 |
| Passifloran 10% | 1 | 1 |
| Buccoxime | 1 | 1 |
| Geraniol super | 40 | 40 |
| Geranyl acetate 60 | 40 | 40 |
| Hedione | 90 | 90 |
| Poivrol | 25 | 25 |
| Ambrocenide 10 | 1 | 1 |
| Globalide | 50 | 50 |
| Triethyl citrate | 25 | 20 |
| Cantryl | 51 | 51 |
| Compounds of the formula (Ia) or (Ib) 10% in TEC | | 5 |

Version B is much more lively in its freshness and finely rounds off the flowery note. The marked soapy note in version A is balanced out by the compounds of the formula (I) or (Ia). The effect is assessed as being particularly clear with compounds VII and XVI.

TABLE 2

Perfume oil P2 (amounts in g)

| Ingredient | Formulation A | Formulation B |
|---|---|---|
| Farenal 1% | 20 | 20 |
| Mandarin Aldehyde 10% | 5 | 5 |
| Florazon | 10 | 10 |
| Leafovert 10% | 20 | 20 |
| Vertocitral | 1 | 1 |
| Bergamot Oil | 100 | 100 |
| Linalyl acetate | 50 | 50 |
| Dihydromyrcenol | 60 | 60 |
| Orange Oil | 25 | 25 |
| Lavandin Oil | 20 | 20 |
| Cassis Base 345BB | 10 | 10 |
| Calone 1951 10% | 30 | 30 |
| Majantol | 45 | 45 |
| Linalool | 60 | 60 |
| Terpineol pure | 20 | 20 |
| Damascone alpha 1% | 20 | 20 |

TABLE 2-continued

Perfume oil P2 (amounts in g)

| Ingredient | Formulation A | Formulation B |
|---|---|---|
| Hexylcinnamicaldehyde alpha | 100 | 100 |
| Hedion HC/30 | 10 | 10 |
| Hedione | 200 | 200 |
| Hexyl salicylate | 20 | 20 |
| Clove Bud Oil | 5 | 5 |
| Kephalis | 5 | 5 |
| Iso E Super | 70 | 70 |
| Terranol | 30 | 30 |
| Polysantol | 5 | 5 |
| Globalide | 20 | 20 |
| Ethylene brassylate | 20 | 20 |
| Farenal 1% | 20 | 20 |
| Mandarin Aldehyde 10% | 5 | 5 |
| Florazon | 10 | 10 |
| Leafovert 10% | 20 | 20 |
| Vertocitral | 1 | 1 |
| Bergamot Oil | 100 | 100 |
| Linalyl acetate | 50 | 50 |
| Dihydromyrcenol | 60 | 60 |
| Orange Oil | 25 | 25 |
| Triethyl citrate | 9 | 8 |
| Cyclogalbanate | 10 | 10 |
| Compounds of the formula (I) or (Ia) 10% in TEC | | 1 |

Version B removes the aggressive green top note. The marine-like accord is integrated into the fragrance by addition of the compounds of the formula (I) or (Ia), giving rise to a gentle spruce effect. The effect is assessed as being particularly clear with the compounds II and XXII.

TABLE 3

Perfume oil P3

| Ingredient | Formulation A | Formulation B |
|---|---|---|
| Aldehyde C11 MOA 10% | 20 | 20 |
| Leafovert 10% | 10 | 10 |
| Cyclogalbanate | 20 | 20 |
| Styrallyl acetate | 15 | 15 |
| Floropal | 10 | 10 |
| Mintonat | 40 | 40 |
| Linalyl acetate | 10 | 10 |
| Dihydromyrcenol | 340 | 340 |
| Citral Melange | 5 | 5 |
| Geranylnitrile Replacement | 5 | 5 |
| Orange Oil | 50 | 50 |
| Mandarin Oil | 10 | 10 |
| Amarocite | 10 | 10 |
| Nerolione 10% DPG | 15 | 15 |
| Lavandin Oil | 25 | 25 |
| Eucalyptol Nat. | 15 | 15 |
| Menthol Laevo Dist. | 100 | 100 |
| Cyclamenaldeyhde | 10 | 10 |
| Linalool | 65 | 65 |
| Citronellol 950 | 20 | 20 |
| Isodamascon 10% | 10 | 10 |
| Hedione | 20 | 20 |
| Isoraldeine 70 | 20 | 20 |
| Anethol supra | 10 | 10 |
| Agrumex HC | 5 | 5 |
| Vertofix | 10 | 10 |
| Iso E Super | 90 | 90 |
| Sandranol | 10 | 10 |
| Aurelione | 20 | 20 |
| Triethyl citrate | 9 | 8 |
| Frescomenthe | 10 | 10 |
| Compounds of the formula (Ia) or (Ib) 10% in DPG | | 1 |

The compounds of the formula (I) or (Ia) push the fresh and minty notes. A transparent, watery effect is the result and makes the composition seem cleaner. The effect is assessed as being particularly marked with the compounds XIV and XXIII.

TABLE 4

Perfume oil P4

| Ingredient | Formulation A | Formulation B |
|---|---|---|
| Octenol-1,3 | 5 | 5 |
| Mintonat | 195 | 195 |
| Linalyl acetate | 80 | 80 |
| Dihydromyrcenol | 35 | 35 |
| Neononyl acetate | 80 | 80 |
| Terpinyl acetate | 100 | 100 |
| Eucalyptus Oil | 80 | 80 |
| Artemisia Oil 10% | 10 | 10 |
| Terpinenol-4 | 5 | 5 |
| Thymol crist. 10% | 10 | 10 |
| Maceal 10% | 10 | 10 |
| Borneol crist. | 60 | 60 |
| Hexylacetate | 5 | 5 |
| Hexylbutyrate | 5 | 5 |
| Linalooloxide | 5 | 5 |
| Tetrahydrolinalool | 90 | 90 |
| Filbertone 10% | 5 | 5 |
| Linalool | 80 | 80 |
| Jessemal | 20 | 20 |
| Eugenol | 10 | 10 |
| Coumarone | 20 | 20 |
| Cyclabute | 25 | 25 |
| Vetival | 10 | 10 |
| Patchouly Oil | 10 | 10 |
| Evernyl | 1 | 1 |
| Isomuscone | 10 | 10 |
| Triethyl citrate | 9 | 6.5 |
| Isooctanone | 25 | 25 |
| Compounds of the formula (I) or (Ia) 10% in DPG | | 2.5 |

Here, the compounds of the formula (I) or (Ia) turn the fragrance in a hereby direction. A sweet impression is the result, the lavender/coumarin note of which seems much more marked. At the same time, the camphor-like note is covered a little. The effect is assessed as being particularly marked with the compounds XV and XXII.

TABLE 5

Perfume oil P5

| Ingredient | Formulation A | Formulation B |
|---|---|---|
| Citral | 15 | 15 |
| Pinen alpha laevo nat. | 10 | 10 |
| Linalool | 100 | 100 |
| Linalool oxide | 3.5 | 3.5 |
| Terpineol alpha | 10 | 10 |
| Geranium chin. | 15 | 15 |
| Rose oxide high cis | 6.5 | 6.5 |
| Citronellol | 390 | 390 |
| Geraniol | 200 | 200 |
| Citronellyl formate | 80 | 80 |
| Geranyl acetate | 8.5 | 8.5 |
| Geranyl butyrate | 10 | 10 |
| Geranyl formate | 65 | 65 |
| Geranyl isobutyrate | 4.5 | 4.5 |
| Geranyl propionate | 20 | 20 |
| Geranyl tiglinate | 10 | 10 |
| Caryophyllene nat. rect. | 7 | 7 |
| Triethyl citrate | 10 | 6.5 |
| Menthone | 35 | 35 |
| Compounds of the formula (I) or (Ia) 10% in TEC | | 3.5 |

The compounds of the formula (I) or (Ia) push the freshness here too. The slightly metallic minty note is distinctly reduced and rounded off. The effect is assessed as being particularly clear with the compounds XX and XXI.

Example 5

Formulation Examples F1 to F11

Perfume oils P1, P2, P3, P4 and P5 made from the above perfume oil examples 1 to 5 were each incorporated separately into the formulations which follow. The odor effects described above for the respective perfume oil were each also observed in the formulations which follow.

TABLE 6

Washing powder (figures in % by weight)

| Material | Chemical name | Function | A | B |
|---|---|---|---|---|
| Sodium metasilicate pentahydrate | Sodium metasilicate pentahydrate | | Ad 100 | Ad 100 |
| Sodium hydrogencarbonate | Sodium hydrogen carbonate | Alkali | 15.0 | 15.0 |
| Sodium percarbonate | Sodium carbonate peroxyhydrate | Bleach | 15.0 | 15.0 |
| Peractive AC Blue | TAED/Na—Carboxymethylcellulose | Activator | 5.00 | 5.00 |
| Genapol OA-080 | Oxo alcohol C14-15, 8EO | Nonionic surfactant | 3.00 | 3.00 |
| Texapon K12 powder | Sodium Lauryl Sulfate C12 | Anionic surfactant | 7.00 | 7.00 |
| Tinopal CBS-X | | Brightener | 0.50 | 0.50 |
| Savinase 6.0 T, Type W | Protease | Enzyme | 0.40 | 0.40 |
| Termamyl 120 T | Alpha-Amylase | Enzyme | 0.30 | 0.30 |
| Sodium sulfate | Sodium Sulfate | Filler | 5.50 | 5.50 |
| Perfume oil P1, P2, P3, P4 or P5 | | Perfume (fragrance) | 0.30 | 0.50 |

TABLE 7

All-purpose cleaner (figures in % by weight)

| Material | Chemical name | Function | A | B |
|---|---|---|---|---|
| Deionized water | Water | Solvent | Ad 100 | Ad 100 |
| Mergal K9N | 5-Chloro-2-methyl-3-(2H)-isothiazolone and 2-methyl-3-(2H)-isothiazolone | Preservative | 0.1 | 0.1 |
| Trisodium citrate dihydrate | Tri Sodium Citrate Dihydrate | Complexing agent | 3.0 | 3.0 |
| Zetesol NL-2 | Fatty alcohol C12-14-sulfate, Sodium | Anionic surfactant | 30.0 | 30.0 |
| Imbentin C/125/055 | Fatty alcohol C12-C15, 8EO | Nonionic surfactant | 5.0 | 5.0 |
| Ethanol | Ethanol | Solvent | 2.0 | 2.0 |
| Perfume oil P1, P2, P3, P4, or P5 | | Parfum (fragrance) | 0.3 | 0.5 |

TABLE 7

Shampoo (figures in % by weight)

| Material | INCI-Name | A | B |
|---|---|---|---|
| Deionized water | Water | Ad 100 | Ad 100 |
| Plantacare PS 10 | Sodium Laureth Sulfate, Lauryl Glucoside | 20.0 | 20.0 |
| Euperlan PK 771 | Glycol Distearate, Sodium Lauryl Sulfate, Cocamide MEA, Laureth-10 | 6.0 | 6.0 |
| Dragocid Liquid | Phenoxyethanol, Methylparaben, Ethylparaben, Butylparaben, Propylparaben, Isobutylparaben | 0.5 | 0.5 |
| Sodium chloride | Sodium Chloride | 1.4 | 1.4 |
| Citric acid monohydrate crystalline | Citric Acid | 0.1 | 0.1 |
| Perfume oil P1, P2, P3, P4, or P5 | Parfum (fragrance) | 0.5 | 0.8 |

TABLE 8

Shower gel (figures in % by weight)

| Material | INCI-Name | A | B |
|---|---|---|---|
| Deionized water | Water | Ad 100 | Ad 100 |
| Plantacare PS 10 | Sodium Laureth Sulfate, Lauryl Glucoside | 20.0 | 20.0 |
| Dragocid Liquid | Phenoxyethanol, Methylparaben, Ethylparaben, Butylparaben, Propylparaben, Isobutylparaben | 0.5 | 0.5 |
| Sodium chloride | Sodium Chloride | 1.4 | 1.4 |
| Citric acid monohydrate crystalline | Citric Acid | 1.3 | 1.3 |
| Perfume oil P1, P2, P3, P4, or P5 | Parfum (fragrance) | 0.5 | 0.7 |

TABLE 9

Fabric softener (figures in % by weight)

| Material | Chemical name | Function | A | B |
|---|---|---|---|---|
| Deionized water | Water | Solvent | Ad 100 | Ad 100 |
| Rewoquat WE 18 | Dialkylesterammonium ethosulfate | Cationic surfactant | 16.6 | 16.6 |
| Mergal K9N | 5-Chloro-2-methyl-3-(2H)-isothiazolone and 2-methyl-3-(2H)-isothiazolone | Preservative | 0.10 | 0.10 |
| Dow Corning 1520 antifoam | Polydimethylsiloxane | Defoamer | 0.30 | 0.30 |
| Magnesium chloride 1% solution | Magnesium Chloride solution | Bodying agent | 10.00 | 10.00 |
| Perfume oil P1, P2, P3, P4, or P5 | | Fragrance | 0.55 | 0.75 |

TABLE 10

Eau de Cologne/Eau de Toilette (figures in % by weight)

| Ingredients | A | B |
|---|---|---|
| Perfume oil P1, P2, P3, P4, or P5 | 5 | 10 |
| Ethanol | Ad 100 | Ad 100 |
| Water | 18 | 10 |

TABLE 11

Aerosol pump spray (figures in % by weight)

| Ingredients | A | B |
|---|---|---|
| Perfume oil P1, P2, P3, P4, or P5 | 1.0 | 1.5 |
| Ethanol | Ad 100 | Ad 100 |
| Water | 5.0 | 8.0 |
| alpha-Tocopherol | 0.20 | 0.20 |
| Hydroxypropylcellulose | 0.20 | — |
| Rosemary extract, soluble in ethanol | 0.22 | — |
| Cetyl alcohol | 1.00 | 0.50 |

TABLE 12

Shampoo (figures in % by weight)

| Ingredients | A | B | C |
|---|---|---|---|
| Sodium lauryl ether sulfate (e.g. Texapon NSO, from Cognis Deutschland GmbH) | 12 | 12 | 12 |
| Cocamidopropyl betaine (e.g. Dehyton K, from Cognis Deutschland GmbH) | 2 | 2 | 2 |
| Sodium chloride | 1.4 | 1.4 | 1.4 |
| Citric acid | 1.3 | 1.3 | 1.3 |
| Phenoxyethanol, methyl-, ethyl-, butyl- and propylparaben | 0.5 | 0.5 | 0.5 |
| Perfume oil P1, P2, P3, P4, or P5 | 0.3 | 0.5 | 0.7 |
| Water | Ad 100 | Ad 100 | Ad 100 |

TABLE 13

Washing powder (figures in % by weight)

| Ingredients | A | B | C |
|---|---|---|---|
| Linear Na alkylbenzenesulfonate | 8.8 | 8.8 | 8.8 |
| Ethoxylated fatty alcohol C12-18 (7 EO) | 4.7 | 4.7 | 4.7 |
| Na soap | 3.2 | 3.2 | 3.2 |
| DOW CORNING(R) 2-4248S POWDERED ANTIFOAM, silicone oil on zeolite as carrier material | 3.9 | 3.9 | 3.9 |
| Zeolite 4A | Ad 100 | Ad 100 | Ad 100 |
| Na carbonate | 11.6 | 11.6 | 11.6 |
| Na salt of a copolymer of acrylic acid and maleic acid (Sokalan CP5) | 2.4 | 2.4 | 2.4 |
| Na silicate | 3.0 | 3.0 | 3.0 |
| Carboxymethylcellulose | 1.2 | 1.2 | 1.2 |
| Dequest 2066([[(Phosphonomethyl)imino]bis[(ethylenenitrilo)bis(methylene)]]tetrakisphosphonic acid, sodium salt) | 2.8 | 2.8 | 2.8 |
| Optical brightener | 0.2 | 0.2 | 0.2 |
| Na sulfate | 6.5 | 6.5 | 6.5 |
| Protease | 0.4 | 0.4 | 0.4 |
| Sodium perborate tetrahydrate | 21.7 | 21.7 | 21.7 |
| Perfume oil P1, P2, P3, P4, or P5 | 0.25 | 0.35 | 0.5 |
| EDTA | 1.0 | 1.0 | 1.0 |

TABLE 14

Liquid washing composition (figures in % by weight)

| Ingredients | A |
|---|---|
| Deionized water | 39.9 |
| Optical brightener | 0.10 |
| Coconut fatty acids (C12-C18) | 7.5 |
| Potassium hydroxide 50% solution | 4.3 |
| Propane-1,2-diol | 5.00 |
| Fatty alcohols C12-C15, 8 EO | 12.0 |
| Na salt of secondary alkylsulfonates (C13-C17) | 17.0 |
| Triethanolamine | 2.0 |
| Trisodium citrate dihydrate | 5.0 |
| Dequest 2066([[(Phosphonomethyl)imino]bis[(ethylenenitrilo)bis(methylene)]]tetrakisphosphonic acid, sodium salt) | 3.0 |
| Ethanol | 3.0 |
| Enzymes | 0.7 |
| Perfume oil P1, P2, P3, P4, or P5 | 0.5 |

TABLE 15

Liquid washing composition concentrate (figures in % by weight)

| Ingredients | A |
|---|---|
| Deionized water | 13.4 |
| Coconut fatty acids (C12-C18) | 10.0 |
| Fatty alcohols C12-C15, 8 EO | 26.0 |
| Na salt of secondary alkylsulfonates (C13-C17) | 26.5 |
| Triethanolamine | 8.5 |
| Na salt of fatty alcohol sulfates C12-C14 | 3.0 |
| Ethanol | 5.5 |
| Urea | 4.5 |
| Enzymes | 0.9 |
| Citric acid | 1.0 |
| Perfume oil P1, P2, P3, P4, or P5 | 0.7 |

Example 6

Stability Test

The fabric softener F5 and Eau de Cologne F6 from example 5 were stored in order to assess the stability of the formulation and the fragrance note after the storage time. The results are shown in table 16:

TABLE 16

| | Stabilities | | | |
|---|---|---|---|---|
| | 4 weeks | | 8 weeks | |
| | 23° C. | 40° C. | 23° C. | 40° C. |
| F5 without perfume oils of the invention | Formulation stable, Fragrance in a herby direction | Formulation stable, Fragrance in a herby direction | Formulation stable, Camphor-like note becomes prominent | Formulation stable, Camphor-like note becomes prominent |
| F5 from example 5 | Formulation stable, Lavender/coumarin note more marked, sweetish impression | Formulation stable, Lavender/coumarin note marked, sweetish impression | Formulation stable, Lavender/coumarin note present, sweetish impression | Formulation stable, Lavender/coumarin note present, sweetish impression |
| F6 without perfume oils of the invention | Formulation stable, Fresh, light-colored, slightly metallic | Formulation stable, Fresh, metallic | Formulation stable, Fresh, light-colnred, metallic | Formulation stable, light-colored, metallic |
| F6 from example 5 | Formulation stable, Fresh, light-colored, minty note, not metallic | Formulation stable, Fresh, light-colored, minty note slightly reduced, not metallic | Formulation stable, Fresh, light-colored, minty note slightly reduced, not metallic | Formulation stable, Fresh, light-colored, minty note distinctly reduced, slightly metallic |

The invention claimed is:

1. An odorant mixture, comprising:
   (a) methyl 2-cyclopent-2-en-1-ylacetate,
   (b) an odorant selected from ketones and/or nitriles having a molecular weight of from 140 g/mol to 170 g/mole, and
   (c) an odorant selected from ketones, esters, lactones and acetals having a molecular weight of from 220-320 g/mole.

2. The odorant mixture as claimed in claim 1, wherein the
   (i) mass ratio of the total amount of odorant (b) to methyl 2-cyclopent-2-en-1-ylacetate (a) is not less than 99:1, and/or
   (ii) the mass ratio of the total amount of odorant (c) to methyl 2-cyclopent-2-en-1-ylacetate (a) is not less than 99:1,
   based in each case on the total amount of all odorants in the individual groups of methyl 2-cyclopent-2-en-1-ylacetate (a), and odorants (b) and (c), based on the overall odorant mixture.

3. A perfume oil comprising the mixture as claimed in claim 1.

4. The odorant mixture as claimed in claim 1, in an amount effective for generation, imparting, modification or enhancement of a fruity odor in the apple, pear, pineapple, banana and strawberry direction.

5. A method of producing an odorant mixture as claimed claim 1, comprising the following steps:
   (a) providing methyl 2-cyclopent-2-en-1-ylacetate,
   (b) providing at least one further odorant, selected from the group consisting of ketones and nitriles having a molar mass of 140 g/mol to 170 g/mol,
   (c) providing at least one or more further odorant selected from the group consisting of lactones and acetals having a molar mass in the range from 220 g/mol to 320 g/mol and mixtures thereof, and
   (d) mixing the constituents (a), (b) and (c).

6. A method of enhancing the natural freshness and/or impression and/or for masking or reducing fatty and/or metallic notes of different odorants, comprising:
   mixing the odorants (b) and (c) with an amount of methyl 2-cyclopent-2-en-1-ylacetate (a) according to claim 1, sufficient to enhance the natural freshness and/or impression of the odorants, and/or mask or reduce fatty and/or metallic notes.

7. The method as claimed in claim 6, wherein the odorants (b) and (c) are
   (b) selected from the group consisting of nitriles having a molar mass of 140 g/mol to 170 g/mol, and
   (c) selected from the group consisting of lactones and acetals having a molar mass in the range from 220 g/mol to 320 g/mol.

8. The method as claimed in claim 6, wherein the mass ratio of the total amount of odorants (b) and (c) to methyl 2-cyclopent-2-en-1-ylacetate (a) is not less than 99:1.

9. A perfumed product comprising an odorant mixture as claimed in claim 1, in a sensorially effective amount.

10. The perfumed product as claimed in claim 9, selected from perfume extracts, eau de parfums, eau de toilettes, aftershaves, eau de colognes, pre-shave products, splash colognes, perfumed refreshing tissues, acidic, alkaline and neutral cleaning products, textile fresheners, ironing aids, liquid laundry detergents, pulverulent laundry detergents, laundry pretreatment products, laundry softeners, laundry soaps, laundry tablets, disinfectants, surface disinfectants, air fresheners, aerosol sprays, waxes and polishes, personal care products, hand creams and lotions, foot creams and lotions, hair removal creams and lotions, aftershave creams and lotions, tanning creams and lotions, haircare products, deodorants and antiperspirants, decorative cosmetics products, candles, lamp oils, incense sticks, insecticides, repellents and fuels.

11. The perfumed product as claimed in claim 9, wherein the proportion of the odorant mixture in the perfumed product is 0.01% to 10% by weight, based on the total mass of the perfumed product.

12. The perfumed product of claim 9, wherein the odorant mixture comprises a perfume oil.

* * * * *